US011407833B2

United States Patent
Lee et al.

(10) Patent No.: US 11,407,833 B2
(45) Date of Patent: Aug. 9, 2022

(54) ANTI-VISTA ANTIBODY AND USE THEREOF

(71) Applicant: PHARMABCINE INC., Daejeon (KR)

(72) Inventors: Youngae Lee, Daejeon (KR); Sang Soon Byun, Daejeon (KR); Jung Min Ha, Gyeonggi-do (KR); Sungho Ahn, Songpa-gu (KR); Keunhee Oh, Chungcheongbuk-do (KR); Weon Sup Lee, Daejeon (KR); MiJu Park, Gyeonggi-do (KR); Eun Hee Lee, Chungcheongnam-do (KR); Do-yun Kim, Daejeon (KR); Jin-San Yoo, Daejeon (KR)

(73) Assignee: PHARMABCINE INC., Daejeon (KR)

( * ) Notice: Subject to any disclaimer, the term of this patent is extended or adjusted under 35 U.S.C. 154(b) by 107 days.

(21) Appl. No.: 16/757,156

(22) PCT Filed: Oct. 22, 2018

(86) PCT No.: PCT/KR2018/012494
§ 371 (c)(1),
(2) Date: Apr. 17, 2020

(87) PCT Pub. No.: WO2019/078699
PCT Pub. Date: Apr. 25, 2019

(65) Prior Publication Data
US 2020/0407449 A1 Dec. 31, 2020

(30) Foreign Application Priority Data
Oct. 20, 2017 (KR) .................. 10-2017-0136632

(51) Int. Cl.
C07K 16/28 (2006.01)
A61P 35/00 (2006.01)
C12N 15/79 (2006.01)

(52) U.S. Cl.
CPC .......... *C07K 16/2827* (2013.01); *A61P 35/00* (2018.01); *C12N 15/79* (2013.01); *C07K 16/2818* (2013.01); *C07K 2317/565* (2013.01)

(58) Field of Classification Search
CPC .......... C07K 16/2827; C07K 16/2818; C07K 16/28; C07K 2317/565; C07K 2317/21;
(Continued)

(56) References Cited

FOREIGN PATENT DOCUMENTS

| CA | 2935378 A1 | 7/2015 |
|----|-----------|--------|
| JP | 2017502667 A | 1/2017 |

(Continued)

OTHER PUBLICATIONS

Boger, C., et al (2017) The novel negative checkpoint regulator VISTA is expressed in gastric carcinoma and associated with PD-L1/PD-1: A future perspective for a combined gastric cancer therapy Oncoimmunology 6(4); e1293215 (8 pages) (Year: 2017).*
(Continued)

*Primary Examiner* — Joanne Hama
*Assistant Examiner* — Audrey L Buttice
(74) *Attorney, Agent, or Firm* — Elmore Patent Law Group, P.C.; Joseph C. Zucchero; Carolyn S. Elmore

(57) ABSTRACT

The present invention relates to an anti-VISTA antibody or an antigen binding fragment thereof, a nucleic acid coding for the same, a vector carrying the nucleic acid, a cell transformed with the vector, a method for preparing the antibody or an antigen binding fragment thereof, a composition for prevention or treatment of autoimmune disease, comprising the same antibody, and a composition for concurrent administration in combination with a PD-1 antibody or PD-L1 antibody.

8 Claims, 7 Drawing Sheets

Specification includes a Sequence Listing.

(58) Field of Classification Search
CPC ............ C07K 2317/33; C07K 2317/92; C07K 2317/73; C07K 2317/622; A61P 35/00; A61P 37/00; C12N 15/79; A61K 2039/505; A61K 2039/507; A61K 39/00
See application file for complete search history.

(56) References Cited

FOREIGN PATENT DOCUMENTS

| KR | 10-2016-0124086 A | 10/2016 |
|---|---|---|
| KR | 10-2016-0129698 A | 11/2016 |
| KR | 10-2017-0087500 A | 7/2017 |
| WO | 2014190356 A2 | 11/2014 |
| WO | 2015097536 A2 | 7/2015 |
| WO | 2016094837 A2 | 6/2016 |
| WO | 2016207717 A1 | 12/2016 |
| WO | 2017/175058 A1 | 10/2017 |
| WO | 2017/181109 A1 | 10/2017 |

OTHER PUBLICATIONS

Liu, J., et al (2015) Immune-checkpoint proteins VISTA and PD-1 nonredundantly regulate murine T-cell responses PNAS 112(21) 6682-6687 (Year: 2015).*

Cuzick, J. (2017) Preventative therapy for cancer Lancet Oncol 18; e472-482 (Year: 2017).*

Emmons, K. and G. Colditz (2017) Realizing the Potential of Cancer Prevention—The Role of Implementation Science N Engl J Med 376(10); 1-7 (Year: 2017).*

Office Action dated Mar. 4, 2021 in Canadian Application No. 3,079,652.

Office Action dated May 18, 2021 in Japanese Application No. 2020-542518.

Bharaj, P. et al., "Characterization of Programmed Death-1 Homologue-1 (PD-1H) Expression and Function in Normal and HIV Infected Individuals", PLOS ONE, 9(10); e109103, Oct. 2014, 1-10.

Jiang, X. et al., "Abstract 2085: Development of a mechanism-basedpharmacokinetic/pharmacodynamic model tocharacterize tumor killing effect of an anti-VISTAmonoclonal antibody in tumor bearing mice", AACR 107th Annual Meeting 2016; Apr. 16-20, 2016; New Orleans, LA, DOI: 10.1158/1538-7445.AM2016-2085.

Flies, D. B., et al., "Cutting Edge: A Monoclonal Antibody Specific for the Programmed Death-1 Homolog Prevents Graft-versus-Host Disease in Mouse Models," The Journal of Immunology, 2011, 187: 1537-1541.

Lemercier, I., et al., "VISTA regulates the development of protective anti-tumor immunity," Cancer Res., Apr. 1, 2014;74(7): 1933-1944.

* cited by examiner

[Figure 1]
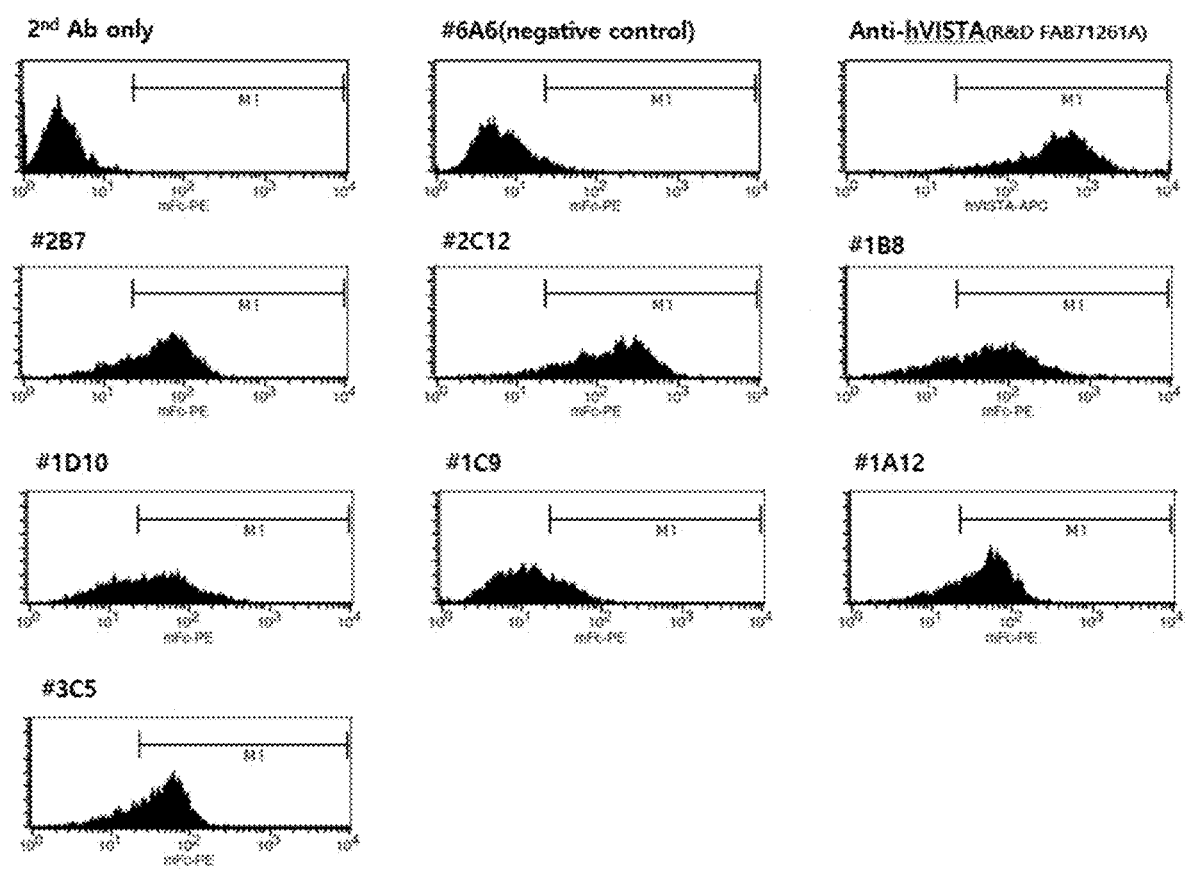

【Figure 2】
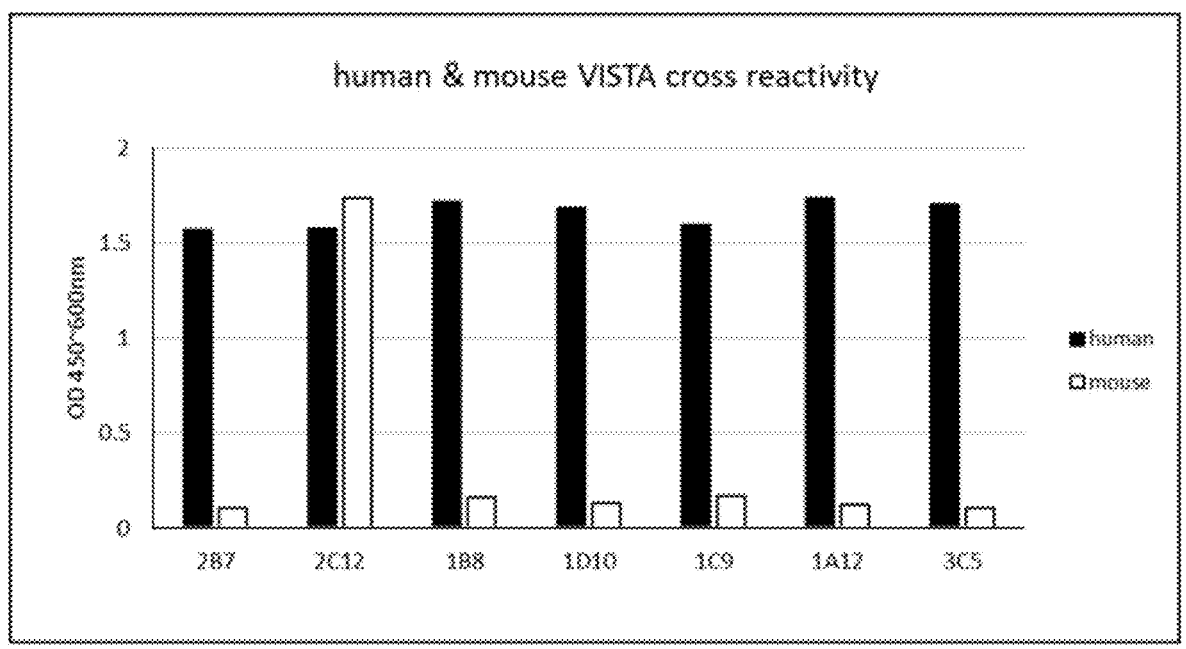

[Figure 3]
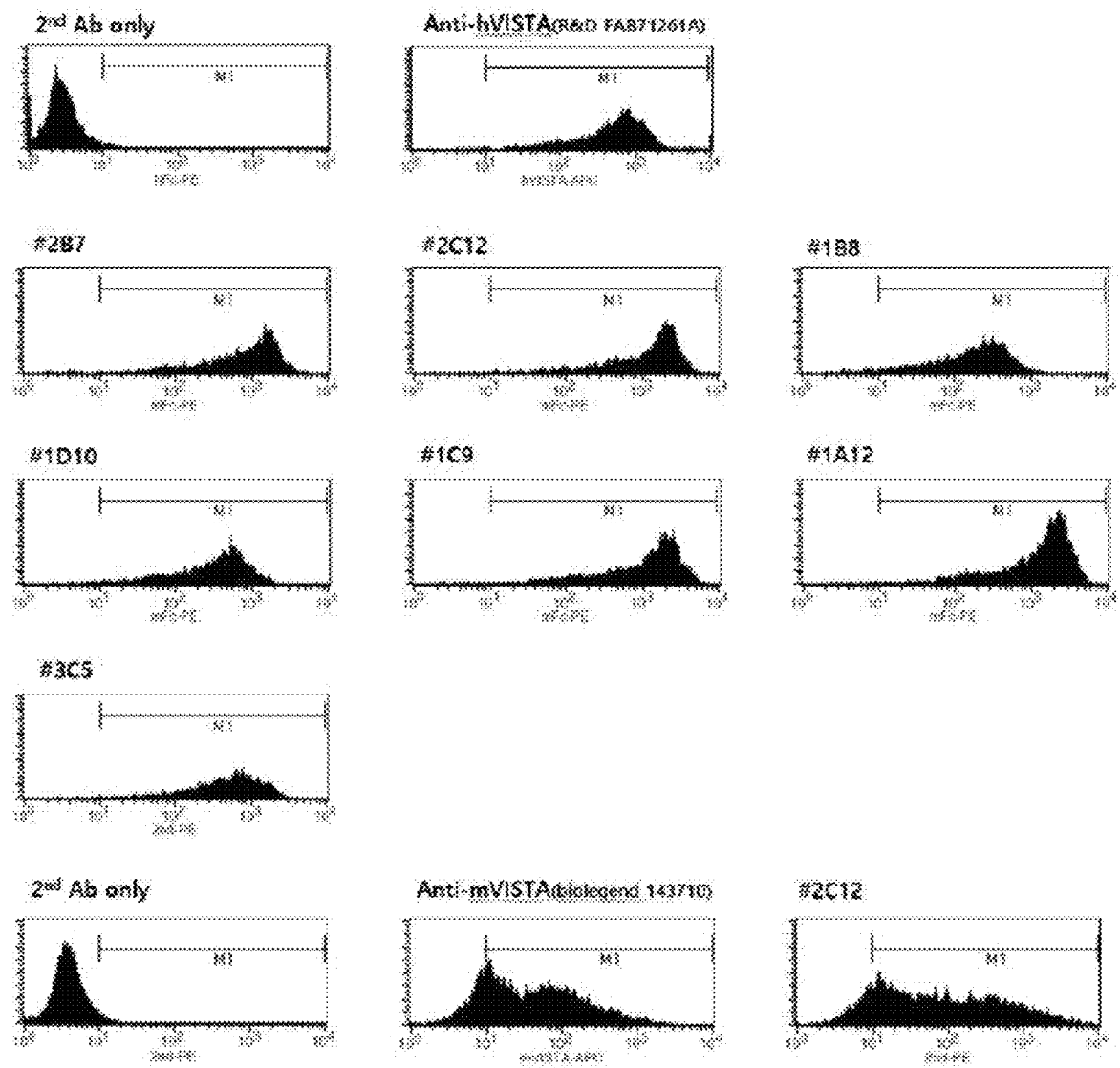

【Figure 4】
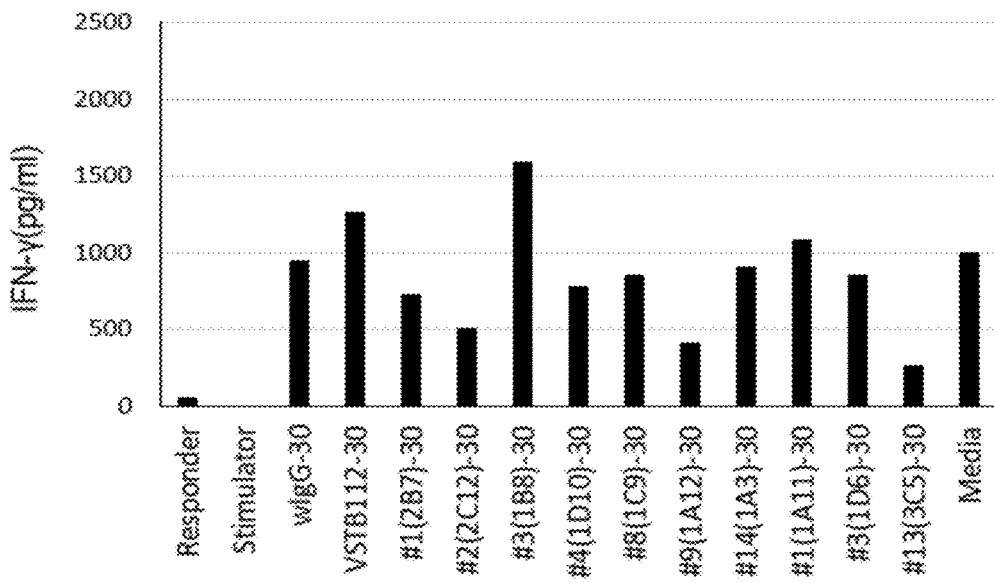
【Figure 5】
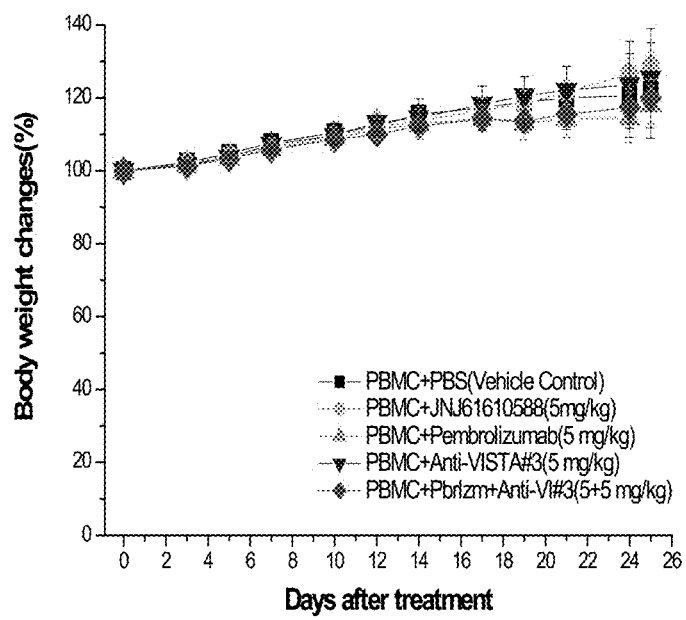

[Figure 6]
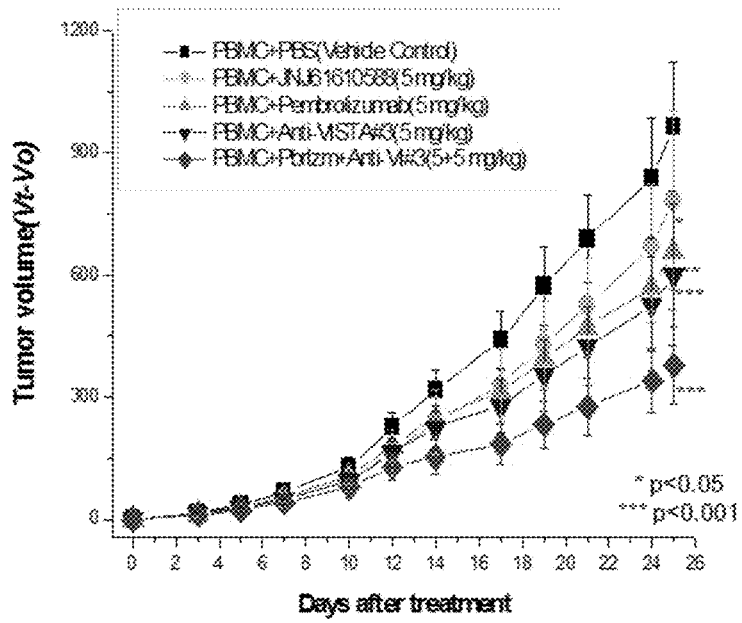
[Figure 7]
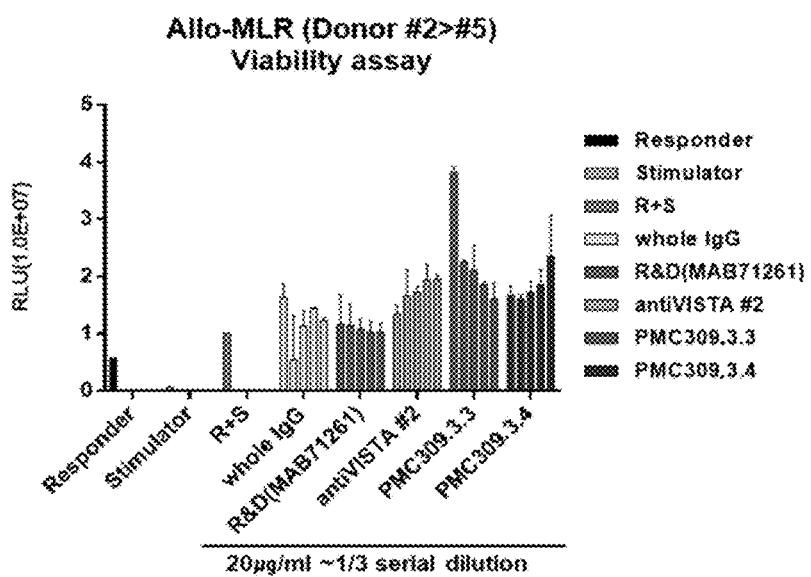

【Figure 8】
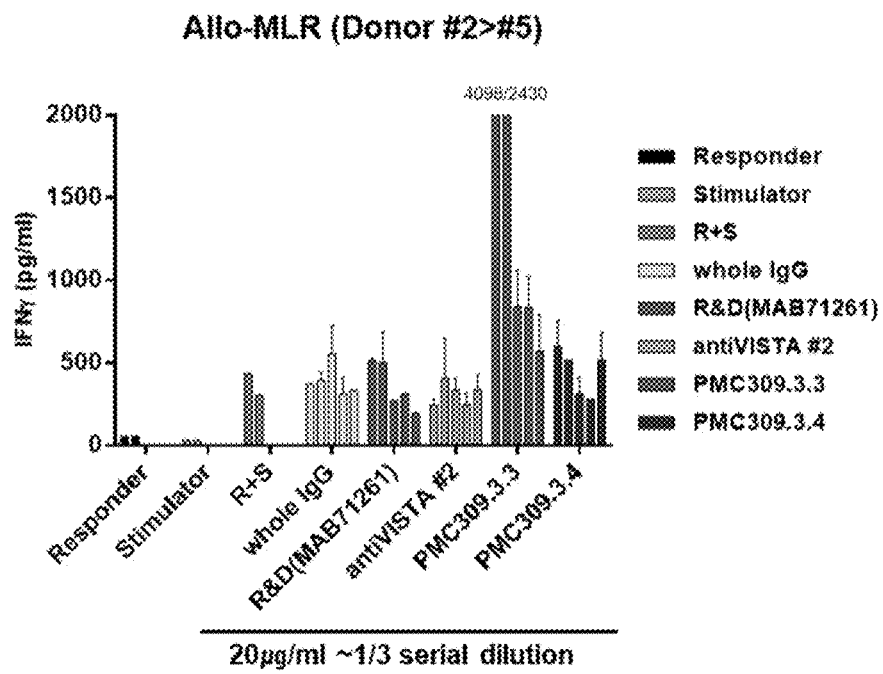
【Figure 9】
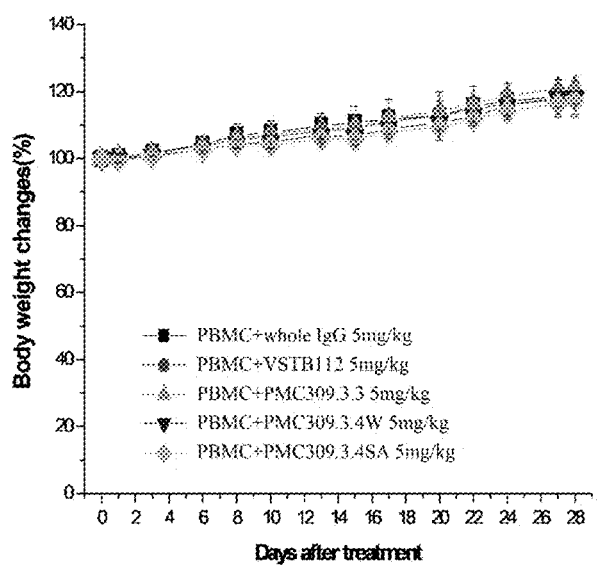

[Figure 10]
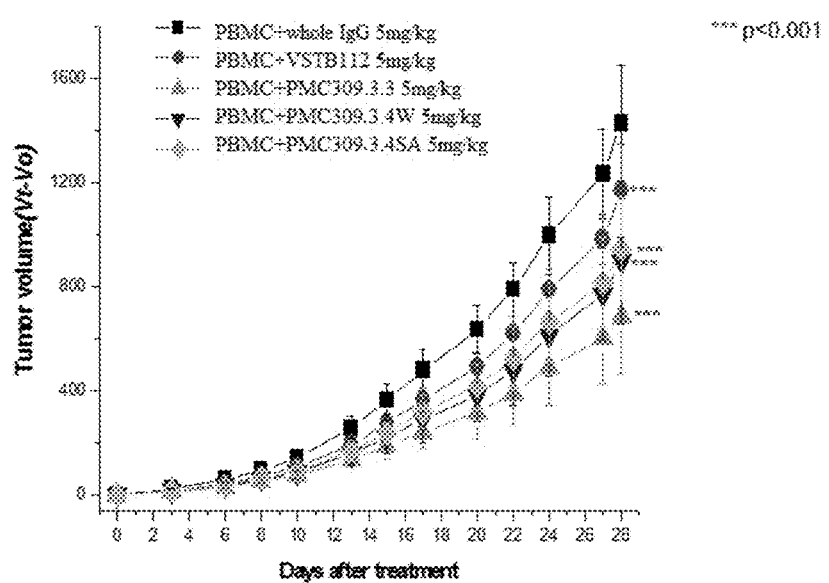

ANTI-VISTA ANTIBODY AND USE THEREOF

TECHNICAL FIELD

The present invention relates to an anti-VISTA antibody or an antigen-binding fragment thereof, a nucleic acid encoding the same, a vector including the nucleic acid, a cell transformed with the vector, a method of preparing the antibody or antigen-binding fragment thereof, a composition including the same for preventing or treating an autoimmune disease, and a composition including the same for administration in combination with a PD-1 antibody or PD-L1 antibody.

BACKGROUND ART

The immune system is a network system involving cells and tissues to respond to foreign pathogens. The immune system for responding to non-self antigens that are repeatedly encountered is broadly classified into a B-cell response using antibodies and a T-cell response that is mediated by cells. In addition to these, there are immune systems that can respond immediately to pathogens, and cells such as macrophages, NK cells and neutrophils are directly involved in removing antigens. As for the immune system, clonal selection or the like acts at the beginning of individual development to prevent the immune system from acting on a self antigen. However, the immune system may often act on self antigens, which may cause disease.

Rheumatoid arthritis is a typical autoimmune disease. Various studies have shown that such an immune evasion mechanisms act even in tumors. The immune evasion mechanism can suppress or increase immunity to antigens by suppressing or promoting the activity of immune cells. Substances involved in this factor are called "immune checkpoints". Recently, various attempts have been made to treat tumors by interfering with immunosuppressive functions on these tumors or by further strengthening factors involved in immune activity.

Since antibodies blocking against CTLA-4 (cytotoxic T-lymphocyte-associated antigen 4), which is an immune checkpoint, were first applied to patients with malignant melanoma in 2010 and a therapeutic effect thereof in about 20% of patients was clearly demonstrated, a new therapeutic approach for treating cancer by enhancing the anti-cancer immune response by inhibiting the action thereof using a therapeutic antibody targeting the immune checkpoint, which functions as a negative immune regulator, has emerged.

Subsequently, the developed anti-PD-1 or anti-PD-L1 antibody exhibited a better effect than the anti-CTLA-4 antibody, and in particular, exhibited a significant reduction in severe side effects occurring in patients undergoing treatment with the CTLA-4 antibody, thus being very actively used in malignant melanoma, non-small cell lung cancer and bladder cancer.

In particular, anti-cancer immunotherapy has been selected occasionally to date for patients for whom conventional cancer treatment methods such as surgery, anti-cancer drugs and radiation therapy have failed, but has increasingly come to be selected as a principal treatment modality based on the development of anti-PD-1/PD-L1 antibodies having reduced side effects, and is actively applied to clinical trials within the treatment scope expanded to various carcinomas not responding to conventional therapeutic agents, such as gastric cancer and liver cancer.

PD-1-targeting therapeutic agents have a mechanism to activate immune surveillance of T-cells, and PD-L1 is a ligand of PD-1 and binds to PD-L1 expressed in tumor cells to interfere with immunosuppression by T-cells and thereby provide anticancer activity. To further maximize this activity, a composition having an immunosuppressive mechanism that does not overlap PD-1/PD-L1 is required. Combination therapy, in which these substances are used together with conventional therapeutic agents, is expected as a very useful tool in improving the treatment efficacy of tumor patients.

VISTA (V-domain-containing Ig Suppressor of T-cell Activation) is a recently identified immune checkpoint substance that is known to directly inhibit the activity of T-cells. VISTA is consistently expressed in hematopoietic compartments, is expressed at the highest level in myeloid family cells, and is expressed at relatively low levels in $CD4^+$, $CD8^+$ T cells and $Foxp3^+$ $CD4^+$ regulatory T cells. VISTA is expressed in most immune cells, including T cells, but is known to be expressed at the highest level in myeloid cells. Therefore, the molecule that suppresses VISTA has a target point different from PD-1 or PD-L1, which can be expected to enhance efficacy in combination therapy with PD-1/PD-L1 therapeutic agents.

VISTA is structurally similar to the TIM family in that it has an extracellular immunoglobulin V (IgV) domain, and human and mouse VISTA amino acid sequences are found to have a homology of approximately 90% therebetween. Some experiments showed that VISTA inhibits proliferation of T-cells and the expression of cytokines based on, as a ligand, an antibody-presenting cell (APC) expressing the entire amino acid sequence of VISTA or VISTA-Fc having the extracellular domain of VISTA binding to the Fc portion of the antibody heavy chain. In addition, VISTA-specific antibodies are known to increase the severity of disease in an autoimmune encephalomyelitis model, and also to increase anti-tumor immune activity (Le Mercier I, et al., 2014).

It is also possible to develop a therapeutic agent for tumor suppression using the immunosuppressive activity of VISTA, but it is also possible to develop a therapeutic agent for GvHD (graft-versus-host disease) and autoimmune diseases by further increasing the immunosuppressive activity of VISTA. For example, antibodies against mouse VISTA were found to suppress GvHD induced by wild-type T-cells (Files, D B et al., 2011). This indicates that the activity of the antibody can act as an agonist or an antagonist depending on the epitope. Therefore, antibodies having two functions may be selected as antibodies against VISTA.

Under this technical background, the present inventors have tried to develop anti-VISTA antibodies. As a result, the present inventors developed an anti-VISTA antibody that has the desired binding ability to VISTA, and found that the anti-VISTA antibody can serve as a targeted anti-cancer agent or autoimmune disease therapeutic agent. Based on this finding, the present invention has been completed.

DISCLOSURE

Technical Problem

It is one object of the present invention to provide a novel antibody against VISTA or an antigen-binding fragment thereof.

It is another object of the present invention to provide a nucleic acid encoding the antibody or an antigen-binding fragment thereof.

It is another object of the present invention to provide a vector including the nucleic acid, a cell transformed with the vector, and a method of producing the same.

It is another object of the present invention to provide a composition including the antibody or an antigen-binding fragment thereof for preventing or treating a tumor, a cancer or an autoimmune disease.

It is another object of the present invention to provide a composition including the antibody or an antigen-binding fragment thereof for administration in combination with a PD-1 antibody or a PD-L1 antibody.

Technical Solution

In accordance with one aspect of the present invention, the above and other objects can be accomplished by the provision of an antibody or an antigen-binding fragment thereof binding to V-domain Ig suppressor of T-cell activation (VISTA) including: a heavy-chain variable region including: a heavy-chain CDR1 selected from the group consisting of SEQ ID NOS: 1, 7, 13 and 19;

a heavy-chain CDR2 selected from the group consisting of SEQ ID NOS: 2, 8, 14 and 20; and a heavy-chain CDR3 selected from the group consisting of SEQ ID NOS: 3, 9, 15 and 21; and a light-chain variable region including: a light-chain CDR1 selected from the group consisting of SEQ ID NOS: 4, 10, 16 and 22;

a light-chain CDR2 selected from the group consisting of SEQ ID NOS: 5, 11, 17 and 23; and a light-chain CDR3 selected from the group consisting of SEQ ID NOS: 6, 12, 18, 24, and 34 to 40.

In another aspect of the present invention, provided is a nucleic acid encoding the antibody or an antigen-binding fragment thereof.

In another aspect of the present invention, provided is a vector including the nucleic acid.

In another aspect of the present invention, provided is a cell transformed with the vector.

In another aspect of the present invention, provided is a method of producing the antibody or antigen-binding fragment thereof including: (a) culturing the cell; and (b) recovering an antibody or antigen-binding fragment thereof from the cultured cell.

In another aspect of the present invention, provided is a composition including the antibody or an antigen-binding fragment thereof as an active ingredient for preventing or treating a tumor, a cancer or an autoimmune disease. In another aspect of the present invention, provided is a method of preventing or treating a tumor, a cancer or an autoimmune disease including administering the antibody or antigen-binding fragment thereof to a patient with a tumor, a cancer or autoimmune disease. In another aspect of the present invention, provided are the use of the antibody or antigen-binding fragment thereof for the inhibition of the immunosuppressive mechanism of VISTA and the use of the antibody or antigen-binding fragment thereof for the prevention or treatment of a tumor, a cancer or the use of the antibody or antigen-binding fragment thereof for the improvement of the immunosuppressive ability of VISTA and the use of the antibody or antigen-binding fragment thereof for the prevention or treatment of an autoimmune disease.

In another aspect of the present invention, provided is a composition including the antibody or antigen-binding fragment thereof for administration in combination with a PD-1 antibody or a PD-L1 antibody. In another aspect of the present invention, provided is a method of preventing or treating a tumor or a cancer including administering the antibody or an antigen-binding fragment thereof in combination with a PD-1 antibody or a PD-L1 antibody to a patient. In another aspect of the present invention, provided are the use of the antibody or antigen-binding fragment thereof for administration in combination with a PD-1 antibody or a PD-L1 antibody to treat a tumor or a cancer.

Advantageous Effects

The anti-VISTA antibody or antigen-binding fragment thereof according to the present invention exhibits desired binding ability to VISTA and can be useful for the prevention or treatment of a targeted cancer/tumor or autoimmune disease. The present invention enables the development of a therapeutic agent having a target point different from that of a conventional therapeutic agent targeting an immune checkpoint, thereby providing combination therapy with the conventional therapeutic agent and single therapy for tumor treatment, and can enhance the activity of checkpoints suppressing immune activity, thereby providing a novel immunosuppressive therapy.

DESCRIPTION OF DRAWINGS

FIG. 1 shows the result of determination of whether or not VISTA-expressing cells bind to monoclonal scFv phages by reacting monoclonal scFv phages with CHO-K1 cells expressing VISTA.

FIG. 2 shows the result of measurement of ELISA to determine whether or not cross-reactivity exists between the selected anti-VISTA antibody and human and mouse VISTA antigens.

FIG. 3 shows the result of determination of the binding ability of selected anti-VISTA antibody to CHO-K1 cells expressing human and mouse VISTA.

FIG. 4 shows the result of measurement of the IFN-γ produced in the human peripheral blood allo-MLR reaction by ELISA.

FIG. 5 shows a result determining that an anti-VISTA antibody administration group loses a significant amount of weight.

FIG. 6 shows a result determining that the anti-VISTA antibody administration group undergoes a significant reduction in tumor weight.

FIG. 7 shows a result determining the effective proliferation of cells through a mixed lymphocyte reaction (MLR) in order to evaluate the function of the optimized anti-VISTA antibody.

FIG. 8 shows a result determining increased cytokine secretion through a mixed lymphocyte reaction (MLR) in order to evaluate the function of the optimized anti-VISTA antibody.

FIG. 9 shows a result determining that an optimized anti-VISTA antibody administration group loses a significant amount of weight.

FIG. 10 shows a result determining that the optimized anti-VISTA antibody administration group undergoes a significant reduction in tumor weight.

BEST MODE

Unless defined otherwise, all technical and scientific terms used herein have the same meanings as appreciated by those skilled in the field to which the present invention pertains. In general, the nomenclature used herein is well-known in the art and is ordinarily used.

Thus, in one aspect, the present invention is directed to an antibody binding to V-domain Ig suppressor of T-cell activation (VISTA) or an antigen-binding fragment thereof including: a heavy-chain variable region including: a heavy-chain CDR1 selected from the group consisting of SEQ ID NOS: 1, 7, 13 and 19;

a heavy-chain CDR2 selected from the group consisting of SEQ ID NOS: 2, 8, 14 and 20; and a heavy-chain CDR3 selected from the group consisting of SEQ ID NOS: 3, 9, 15 and 21; and a light-chain variable region including: a light-chain CDR1 selected from the group consisting of SEQ ID NOS: 4, 10, 16 and 22;

a light-chain CDR2 selected from the group consisting of SEQ ID NOS: 5, 11, 17 and 23; and a light-chain CDR3 selected from the group consisting of SEQ ID NOS: 6, 12, 18, 24, and 34 to 40.

As used herein, the term "antibody" refers to an anti-VISTA antibody that specifically binds to VISTA. The scope of the present invention includes not only a complete antibody specifically binding to VISTA but also an antigen-binding fragment of the antibody molecule.

The term "complete antibody" refers to a structure having two full-length light chains and two full-length heavy chains, wherein each light chain is linked to a corresponding heavy chain by a disulfide bond. The heavy-chain constant region has gamma (γ), mu (μ), alpha (α), delta (δ) and epsilon (ε) types, and is subclassified into gamma 1 (γ1), gamma 2 (γ2), gamma 3 (γ3), gamma 4 (γ4), alpha 1 (γ1) and alpha 2 (α2). The constant region of the light chain has kappa (κ) and lambda (λ) types.

The antigen-binding fragment of an antibody or antibody fragment refers to a fragment that at least has antigen-binding capacity and includes Fab, F(ab'), F(ab')2, Fv and the like. Among the antibody fragments, Fab refers to a structure including a variable region of each of the heavy chain and the light chain, the constant region of the light chain, and the first constant domain (CH1) of the heavy chain, each having one antigen-binding site. Fab' is different from Fab in that it further includes a hinge region including at least one cysteine residue at the C-terminus of the CH1 domain of the heavy chain. F(ab')2 is created by a disulfide bond between cysteine residues in the hinge region of Fab'. Fv is the minimal antibody fragment having only a heavy-chain variable region and a light-chain variable region, and recombinant technology for producing Fv is disclosed in PCT International Publications such as WO 88/10649, WO 88/106630, WO 88/07085, WO 88/07086 and WO 88/09344. Two-chain Fv is a fragment wherein the variable region of the heavy chain and the variable region of the light chain are linked by a non-covalent bond, and single-chain Fv (scFv) is a fragment wherein the variable region of the heavy chain and the variable region of the light chain are generally linked by a covalent bond via a peptide linker therebetween, or are directly linked at the C-terminal, forming a dimer-shaped structure, like the two-chain Fv. Such antibody fragments may be obtained using proteases (e.g., Fab can be obtained by restriction-cleaving the whole antibody with papain, and the F(ab')2 fragment can be obtained by restriction-cleaving the whole antibody with pepsin), and may be prepared using genetic recombination techniques.

In one embodiment, the antibody of the present invention is in an Fv form (for example, scFv) or a complete antibody form. In addition, the heavy-chain constant region may be selected from gamma (γ), mu (u), alpha (α), delta (δ) and epsilon (c) isotypes. For example, the constant region may be gamma 1 (IgG1), gamma 3 (IgG3) or gamma 4 (IgG4). The light-chain constant region may be kappa or lambda.

As used herein, the term "heavy chain" encompasses both a full-length heavy chain, which includes a variable domain (VH) containing an amino acid sequence having a variable region sequence sufficient for imparting specificity to an antigen and three constant domains (CH1, CH2 and CH3), and a fragment thereof. As used herein, the term "light chain" encompasses both a full-length light chain, which includes a variable domain (VL) containing an amino acid sequence having a variable region sequence sufficient for imparting specificity to an antigen and a constant domain (CL), and a fragment thereof.

The antibody of the present invention includes, but is not limited to, monoclonal antibodies, multispecific antibodies, human antibodies, humanized antibodies, chimeric antibodies, single-chain Fvs (scFVs), single-chain antibodies, Fab fragments, F(ab') fragments, disulfide-bond Fvs (sdFVs), anti-idiotypic (anti-Id) antibodies, epitope-binding fragments of such antibodies, and the like.

The term "monoclonal antibody" refers to an identical antibody, excluding possible naturally occurring mutations where an antibody obtained from a population of substantially homogeneous antibodies, that is, each antibody constituting the population, may be present in a small amount. Monoclonal antibodies are highly specific and are thus induced against a single antigenic site. Unlike conventional (polyclonal) antibody preparations that typically include different antibodies directed against different determinants (epitopes), each monoclonal antibody is directed against a single determinant on the antigen.

The term "epitope" refers to a protein determinant to which an antibody can specifically bind. Epitopes usually consist of a group of chemically active surface molecules, such as amino acid or sugar side chains, and generally have not only specific three-dimensional structural characteristics but also specific charge characteristics. Three-dimensional epitopes are distinguished from non-three-dimensional epitopes in that the bond to the former is broken in the presence of a denatured solvent, while the bond to the latter is not broken.

The non-human (e.g., murine) antibody of the "humanized" form is a chimeric antibody containing a minimal sequence derived from non-human immunoglobulin. In most cases, the humanized antibody is a human immunoglobulin (receptor antibody) in which a residue from the hypervariable region of a receptor is replaced with a residue from the hypervariable region of a non-human species (donor antibody) such as a mouse, rat, rabbit or non-human primate having the desired specificity, affinity and ability.

As used herein, the term "human antibody" refers to a molecule derived from human immunoglobulin, in which all of the amino acid sequences constituting the antibody including a complementarity-determining region and a structural region are composed of human immunoglobulins.

The human antibody includes not only a "chimeric" antibody (immunoglobulin) in which the heavy-chain and/or light-chain portions are derived from a certain species, or are identical or homologous to the corresponding sequences in an antibody belonging to a certain antibody class or subclass, but the remaining chain(s) are derived from another species or are identical or homologous to the corresponding sequences in an antibody belonging to another antibody class or subclass, but also a fragment of the antibody that exhibits the desired biological activity.

As used herein, the term "antibody variable domain" refers to light-chain and heavy-chain regions of an antibody molecule including the amino acid sequence of a complementarity-determining region (CDR; i.e., CDR1, CDR2, and CDR3) and a framework region (FR). VH refers to a variable domain of the heavy chain. VL refers to a variable domain of the light chain.

The term "complementarity-determining region" (CDR; i.e., CDR1, CDR2, and CDR3) refers to an amino acid residue of the antibody variable domain that is necessary for antigen binding. Each variable domain typically has three CDR regions, identified as CDR1, CDR2, and CDR3.

In the present invention, the antibody binding to VISTA or an antigen-binding fragment thereof may include a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5 and a light-chain CDR3 of SEQ ID NO: 6, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 33, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 34, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 35, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 36, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 37, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 38, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 39, a heavy-chain variable region including a heavy-chain CDR1 of SEQ ID NO: 1, a heavy-chain CDR2 of SEQ ID NO: 2 and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 40, a heavy-chain variable region including a heavy-chain CDR1 of SEQ ID NO: 7, a heavy-chain CDR2 of SEQ ID NO: 8 and a heavy-chain CDR3 of SEQ ID NO: 9, and a light-chain variable region including a light-chain CDR1 of SEQ ID NO: 10, a light-chain CDR2 of SEQ ID NO: 11, and a light-chain CDR3 of SEQ ID NO: 12, a heavy-chain variable region including a heavy-chain CDR1 of SEQ ID NO: 13, a heavy-chain CDR2 of SEQ ID NO: 14 and a heavy-chain CDR3 of SEQ ID NO: 15, and a light-chain variable region including a light-chain CDR1 of SEQ ID NO: 16, a light-chain CDR2 of SEQ ID NO: 17, and a light-chain CDR3 of SEQ ID NO: 18, or a heavy-chain variable region including a heavy-chain CDR1 of SEQ ID NO: 19, a heavy-chain CDR2 of SEQ ID NO: 20 and a heavy-chain CDR3 of SEQ ID NO: 21, and a light-chain variable region including a light-chain CDR1 of SEQ ID NO: 22, a light-chain CDR2 of SEQ ID NO: 23, and a light-chain CDR3 of SEQ ID NO: 24.

The term "framework region" (FR) refers to a variable-domain residue other than a CDR residue. Each variable domain typically has four FRs, identified as FR1, FR2, FR3, and FR4.

The "Fv" fragment is an antibody fragment containing complete antibody recognition and binding sites. Such a region includes a dimer, for example, scFv, that consists of one heavy-chain variable domain and one light-chain variable domain substantially tightly covalently connected to each other.

A "Fab" fragment contains a variable domain and a constant domain of the light chain and a variable domain and a first constant domain (CH1) of the heavy chain. A F(ab')2 antibody fragment generally includes a pair of Fab fragments covalently linked via a hinge cysteine located therebetween near the carboxyl end thereof.

The "single chain Fv" or "scFv" antibody fragment includes VH and VL domains of the antibody, wherein these domains are present in a single polypeptide chain. The Fv polypeptide may further include a polypeptide linker between the VH domain and the VL domain in order for the scFv to form a desired structure for antigen binding.

The VISTA antibody may include single or double chains. Functionally, the binding affinity of the VISTA antibody ranges from $10^{-3}$ M to $10^{-12}$ M. For example, the binding affinity of the VISTA antibody is $10^{-6}$ M to $10^{-12}$ M, $10^{-7}$ M to $10^{-12}$ M, $10^{-8}$ M to $10^{-12}$ M, $10^{-9}$ M to $10^{-12}$ M, $10^{-3}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-5}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-3}$ M to $10^{-9}$ M, $10^{-6}$ M to $10^{-9}$ M, $10^{-7}$ M to $10^{-9}$ M, $10^{-8}$ M to $10^{-9}$ M, $10^{-5}$ M to $10^{-8}$ M, $10^{-6}$ M to $10^{-8}$ M, $10^{-7}$ M to $10^{-8}$ M, $10^{-5}$ M to $10^{-7}$ M, $10^{-6}$ M to $10^{-7}$ M, or $10^{-3}$ M to $10^{-6}$ M.

The antibody binding to VISTA or an antigen-binding fragment thereof may include a heavy-chain variable region selected from the group consisting of SEQ ID NOS: 25, 27, 29, 31 and 49. In addition, the antibody binding to VISTA or an antigen-binding fragment thereof may include a light-chain variable region selected from the group consisting of SEQ ID NOS: 26, 28, 30, 32, 41 to 48, and 50.

In a specific embodiment according to the present invention, the antibody binding to VISTA or the antigen-binding fragment thereof may include: the heavy-chain variable region of SEQ ID NO: 25 and the light-chain variable region of SEQ ID NO: 26;

the heavy-chain variable region of SEQ ID NO: 25 and the light-chain variable region of SEQ ID NO: 41;

the heavy-chain variable region of SEQ ID NO: 25 and the light-chain variable region of SEQ ID NO: 42;

the heavy-chain variable region of SEQ ID NO: 25 and the light-chain variable region of SEQ ID NO: 43;

the heavy-chain variable region of SEQ ID NO: 25 and the light-chain variable region of SEQ ID NO: 44;

the heavy-chain variable region of SEQ ID NO: 25 and the light-chain variable region of SEQ ID NO: 45;

the heavy-chain variable region of SEQ ID NO: 25 and the light-chain variable region of SEQ ID NO: 46;

the heavy-chain variable region of SEQ ID NO: 25 and the light-chain variable region of SEQ ID NO: 47;

the heavy-chain variable region of SEQ ID NO: 25 and the light-chain variable region of SEQ ID NO: 48;

the heavy-chain variable region of SEQ ID NO: 25 and the light-chain variable region of SEQ ID NO: 50;

the heavy-chain variable region of SEQ ID NO: 49 and the light-chain variable region of SEQ ID NO: 48;

the heavy-chain variable region of SEQ ID NO: 49 and the light-chain variable region of SEQ ID NO: 50;

the heavy-chain variable region of SEQ ID NO: 27 and the light-chain variable region of SEQ ID NO: 28;

the heavy-chain variable region of SEQ ID NO: 29 and the light-chain variable region of SEQ ID NO: 30; or the heavy-chain variable region of SEQ ID NO: 31 and the light-chain variable region of SEQ ID NO: 32.

"Phage display" is a technique for displaying a mutant polypeptide as a fusion protein with at least a part of a coat protein on the surface of the particle of a phage, for example a fibrous phage. The usefulness of phage display is to rapidly and efficiently classify sequences that bind to target antigens with high affinity in large libraries of randomized protein mutants. Displaying peptides and protein libraries on phages has been used to screen millions of polypeptides in order to identify polypeptides with specific binding properties.

Phage display technology has offered a powerful tool for producing and screening novel proteins that bind to specific ligands (e.g., antigens). Using phage display technology, large libraries of protein mutants can be generated and sequences binding with high affinity to target antigens can be rapidly classified. The nucleic acid encoding mutant polypeptides is fused with a nucleic acid sequence encoding a viral coat protein, e.g., a gene III or gene VIII protein. A monophasic phage display system, in which a nucleic acid sequence encoding a protein or polypeptide is fused with a nucleic acid sequence encoding a part of the gene III protein, has been developed. In the monophasic display system, a fused gene is expressed at a low level, a wild-type gene III protein is also expressed, and thus particle infectivity is maintained.

It is important to demonstrate the expression of peptides on the fibrous phage surface and the expression of functional antibody fragments in the peripheral cytoplasm of *E. coli* for the development of antibody phage display libraries. Libraries of antibody- or antigen-binding polypeptides are produced through a number of methods, for example, methods of modifying a single gene by inserting a random DNA sequence or cloning a related gene sequence. Screening can be performed in the libraries regarding the expression of antibody- or antigen-binding proteins having desired characteristics.

Phage display technology has several advantages over conventional hybridomas and recombinant methods for producing antibodies having desired characteristics. This technique provides the generation of large antibody libraries with a variety of sequences within a short time without using animals. The production of hybridomas and the production of humanized antibodies may require a production time of several months. In addition, since no immunity is required, the phage antibody libraries can generate antibodies against antigens that are toxic or have low antigenicity. The phage antibody libraries can also be used to produce and identify novel therapeutic antibodies.

Techniques for generating human antibodies from immunized or non-immunized human, germline sequences, or naive B cell Ig repertoires using phage display libraries can be used. Naive or non-immunogenic antigen-binding libraries can be produced using various lymphatic tissues.

Techniques for identifying and separating high-affinity antibodies from phage display libraries are important for the separation of new therapeutic antibodies. The separation of high-affinity antibodies from the libraries depends on the size of the libraries, the production efficiency in bacterial cells and the variety of libraries. The size of the libraries is reduced by improper folding of the antibody- or antigen-binding protein and inefficient production due to the presence of the stop codon. Expression in bacterial cells may be inhibited by improper folding of the antibody- or antigen-binding domain. The expression can be improved by alternately mutating residues on the surface of the variable/constant interfaces or the selected CDR residues. The sequence of the framework region is an element that enables proper folding when generating antibody phage libraries in bacterial cells.

It is important to generate various libraries of antibody- or antigen-binding proteins in the separation of high-affinity antibodies. CDR3 regions have often been found to participate in antigen binding. Since the CDR3 region on the heavy chain varies considerably in terms of size, sequence and structural/dimensional morphology, various libraries can be produced using the same.

In a specific embodiment according to the present invention, antibody optimization was performed to enhance the affinity of the anti-VISTA antibody clone 1B8, and random mutations were introduced into the light-chain CDR3 and heavy-chain CDR3 of 1B8 and biopanning was performed using a mutant scFv phage library. As a result, 8 types of optimized clones including at least one light-chain variable region CDR3 selected from the group consisting of SEQ ID NOS: 33 to 40 were obtained.

Also, diversity can be created by randomizing the CDR regions of variable heavy and light chains using all 20 amino acids at each position. The use of all 20 amino acids results in production of antibody sequences having increased diversity and an increased chance of identifying new antibodies.

The antibody or antibody fragment of the present invention may include the sequence of the antibody mentioned herein as well as biological equivalents thereto, as long as it can specifically recognize VISTA. For example, additional variations can be made to the amino acid sequence of the antibody in order to further improve the binding affinity and/or other biological properties of the antibody. Such variations include, for example, deletion, insertion and/or substitution of the amino acid sequence residues of the antibody. Such amino acid variations are based on the relative similarity of amino acid side chain substituents, such as the hydrophobicity, hydrophilicity, charge and size thereof. It can be seen through analysis of the size, shape and type of amino acid side chain substituents that all of arginine, lysine and histidine are positively charged residues; alanine, glycine and serine have similar sizes; and phenylalanine, tryptophan and tyrosine have similar shapes. Thus, based on these considerations, arginine, lysine and histidine;

alanine, glycine and serine; and phenylalanine, tryptophan and tyrosine are considered to be biologically functional equivalents.

When taking into consideration variations having biologically equivalent activity, the antibody or a nucleotide molecule encoding the same according to the present invention is interpreted to include a sequence having substantial identity with the sequence set forth in the sequence number. The term "substantial identity" means that a sequence has a homology of at least 90%, most preferably a homology of at least 95%, at least 96%, at least 97%, at least 98% or at least 99%, when aligning the sequence of the present invention and any other sequence so as to correspond to each other as much as possible and analyzing the aligned sequence using algorithms commonly used in the art. Alignment methods for sequence comparison are well-known in the art. The NCBI Basic Local Alignment Search Tool (BLAST) is accessible through NCBI or the like, and can be used in conjunction with sequence analysis programs such as BLASTP, BLASTM, BLASTX, TBLASTN and TBLASTX over the Internet. BLAST is available at www.ncbi.nlm.nih.gov/BLAST/. A method of comparing sequence homology using this program can be found at www.ncbi.nlm.nih.gov/BLAST/blast_help.html.

Based on this, the antibody or antigen-binding fragment thereof according to the present invention can have a homology of 90%, 91%, 92%, 93%, 94%, 95%, 96%, 97%, 98%, or 99% or more compared to the sequence disclosed herein or the entirety thereof. Such homology can be determined through sequence comparison and/or alignment by methods known in the art. For example, the percentage sequence homology of the nucleic acid or protein according to the present invention can be determined using a sequence comparison algorithm (i.e., BLAST or BLAST 2.0), manual alignment, or visual inspection.

In another aspect, the present invention is directed to a nucleic acid encoding the antibody or an antigen-binding fragment thereof.

By isolating the nucleic acid encoding the antibody or antigen-binding fragment thereof according to the present invention, an antibody or antigen-binding fragment thereof can be produced in a recombinant manner. The nucleic acid is isolated and inserted into a replicable vector, followed by further cloning (amplification of DNA) or further expression. Based on this, in another aspect, the present invention is directed to a vector including the nucleic acid.

The term "nucleic acid" is intended to encompass both DNA (gDNA and cDNA) and RNA molecules, and a nucleotide, which is a basic constituent unit of a nucleic acid, includes naturally derived nucleotides as well as analogues thereof, wherein sugar or base moieties are modified. The sequence of the nucleic acid encoding heavy- and light-chain variable regions of the present invention can vary. Such variation includes addition, deletion, or non-conservative or conservative substitution of nucleotides.

The DNA encoding the antibody can be easily separated or synthesized using conventional procedures (for example, using an oligonucleotide probe capable of specifically binding to DNA encoding heavy and light chains of the antibody). A variety of vectors are obtainable. Vector components generally include, but are not limited to, one or more of the following components: signal sequences, replication origins, one or more marker genes, enhancer elements, promoters, and transcription termination sequences.

As used herein, the term "vector" refers to a means for expressing target genes in host cells, and includes plasmid vectors, cosmid vectors, and viral vectors such as bacteriophage vectors, adenovirus vectors, retroviral vectors and adeno-associated viral vectors. The nucleic acid encoding the antibody in the vector is operably linked to a promoter.

The term "operably linked" means a functional linkage between a nucleic acid expression regulation sequence (e.g., array of the binding site of promoter, signal sequence or transcription regulator) and another nucleic acid sequence, and enables the regulation sequence to regulate the transcription and/or translation of the other nucleic acid sequence.

When a prokaryotic cell is used as a host, it generally includes a potent promoter capable of conducting transcription (such as a tac promoter, lac promoter, lacUV5 promoter, lpp promoter, pLλ promoter, pRλ promoter, racy promoter, amp promoter, recA promoter, SP6 promoter, trp promoter, or T7 promoter), a ribosome-binding site for initiation of translation and a transcription/translation termination sequence. In addition, for example, when a eukaryotic cell is used as a host, it includes a promoter derived from the genome of mammalian cells (e.g., a metallothionein promoter, a β-actin promoter, a human hemoglobin promoter or a human muscle creatine promoter), or a promoter derived from a mammalian virus (e.g., an adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, Moloney virus promoter, Epstein-Barr virus (EBV) promoter, and Rous sarcoma virus (RSV) promoter), and generally has a polyadenylation sequence as a transcription termination sequence.

Optionally, the vector may be fused with another sequence in order to facilitate purification of the antibody expressed therefrom. The sequence to be fused includes, for example, glutathione S-transferase (Pharmacia, USA), maltose-binding protein (NEB, USA), FLAG (IBI, USA), 6× His (hexahistidine; Qiagen, USA) and the like.

The vector includes antibiotic-resistant genes commonly used in the art as selectable markers, and examples thereof include genes conferring resistance to ampicillin, gentamycin, carbenicillin, chloramphenicol, streptomycin, kanamycin, geneticin, neomycin and tetracycline.

In another aspect, the present invention is directed to a cell transformed with the above-mentioned vector. The cell used to produce the antibody of the present invention may be a prokaryote, yeast or higher eukaryotic cell, but is not limited thereto.

Prokaryotic host cells such as *Escherichia coli*, strains of the genus *Bacillus*, such as *Bacillus subtilis* and *Bacillus thuringiensis, Streptomyces* spp., *Pseudomonas* spp. (for example, *Pseudomonas putida*), *Proteus mirabilis* and *Staphylococcus* spp. (for example, *Staphylococcus carnosus*) may be used.

Interest in animal cells is the greatest, and examples of useful host cell lines include, but are not limited to, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, and HT1080.

In another aspect, the present invention is directed to a method of producing the antibody or antigen-binding fragment thereof including: (a) culturing the cell; and (b) recovering an antibody or antigen-binding fragment thereof from the cultured cell.

The cells can be cultured in various media. Any commercially available medium can be used as a culture medium without limitation. All other essential supplements well-known to those skilled in the art may be included in appropriate concentrations. Culture conditions such as temperature and pH are conventionally used with host cells selected for expression, as will be apparent to those skilled in the art.

The recovery of the antibody or antigen-binding fragment thereof can be carried out, for example, by centrifugation or ultrafiltration to remove impurities and purification of the resulting product using, for example, affinity chromatography. Other additional purification techniques such as anion or cation exchange chromatography, hydrophobic interaction chromatography and hydroxyapatite (HA) chromatography may be used.

In another aspect, the present invention is directed to a composition for preventing or treating a tumor or a cancer including the antibody as an active ingredient. The antibody may be IgG or a fragment including a variable region, namely ScFv or Fab. In addition, the variable region of the heavy chain may be IgG1, IgG2, IgG3 or IgG4.

The present invention may provide, for example, a pharmaceutical composition for preventing or treating a tumor or a cancer containing: (a) a pharmaceutically effective amount of the antibody to VISTA or antigen-binding fragment thereof according to the present invention; and (b) a pharmaceutically acceptable carrier. The present invention also relates to a method for preventing or treating a tumor or a cancer including administering the antibody or an antigen-binding fragment thereof according to the present invention to a patient with a tumor or a cancer. The present invention may provide the use of the antibody or antigen-binding fragment thereof for the inhibition of the immunosuppressive mechanism of VISTA and the use thereof for the prevention or treatment of a tumor or a cancer.

Tumors, which are the diseases to which the composition can be applied, include typical tumors or cancers that respond to immunotherapy, as well as tumors or cancers that have not been treated with immunotherapy to date. Non-limiting examples of tumors or cancers that are targets of treatment include melanoma (e.g., metastatic malignant melanoma), kidney cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, head and neck squamous cell carcinoma, liver cancer, ovarian cancer, cervical cancer, thyroid cancer, glioblastoma, glioma, leukemia, lymphoma, and other neoplastic carcinomas. In addition, the tumors or cancers according to the present invention include refractory or recurrent cancers that can be treated using the antibody of the present invention.

In another aspect, the present invention is directed to a composition for preventing or treating an autoimmune disease including the antibody as an active ingredient. The antibody may be IgG or a fragment including a variable region, namely ScFv or Fab. In addition, the variable region of the heavy chain may be IgG1, IgG2, IgG3 or IgG4.

The present invention may provide, for example, a composition for preventing or treating an autoimmune disease, containing: (a) a pharmaceutically effective amount of the antibody to VISTA or antigen-binding fragment thereof according to the present invention; and (b) a pharmaceutically acceptable carrier. The present invention also relates to a method for preventing or treating an autoimmune disease including administering the antibody or an antigen-binding fragment thereof according to the present invention to a patient with an autoimmune disease. The present invention may provide the use of the antibody or antigen-binding fragment thereof for the improvement of the immunosuppressive mechanism of VISTA and the use thereof for the prevention or treatment of an autoimmune disease.

The autoimmune disease may for example include: leukemia; chronic fatigue syndrome; graft-versus-host disease (GVHD); hyperalgesia; inflammatory bowel diseases; neuroinflammatory diseases; ischemia/reperfusion injuries including cerebral ischemia, brain damage resulting from trauma, epilepsy, bleeding or seizures that may cause neurodegeneration; diabetes, for example, type 1 combustible diabetes; multiple sclerosis; eye diseases; pain; pancreatitis; pulmonary fibrosis; rheumatoid diseases such as rheumatoid arthritis, osteoarthritis, juvenile rheumatoid arthritis, seropositive polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjogren's syndrome, rheumatic fever, polychondritis and multiple myalgia, rheumatoid and giant cell arteritis; septic shock; side effects resulting from radiotherapy; systemic lupus erythematosus; temporal mandibular joint disease; thyroiditis and the like.

As used herein, the term "prevention" refers to any action causing the suppression of a cancer or an autoimmune disease or the delay of progression thereof by administration of the composition according to the present invention. The term "treatment" means suppression, alleviation or elimination of the progression of cancer, or suppression, alleviation or elimination of the progress of an autoimmune disease.

In some cases, it is possible to effectively target tumor cells using the antibody in combination with another anti-cancer therapeutic agent, and it is possible to enhance the immune response targeting tumor cells by increasing anti-tumor T cell activity. The antibody may be used in combination with: other anti-neoplastic or immunogenic agents [e.g., attenuated cancer cells, tumor antigens (including recombination proteins, peptides and carbohydrate molecules), antigen transfer cells, for example, tumor-derived antigens or nucleic acids-pulsed dendritic cells, immunostimulating cytokines (e.g., IL-2, IFNα2, and GM-CSF), and cells transfected with genes encoding immunostimulating cytokines (including for example but not limited to GM-CSF)]; standard cancer therapy (e.g. chemotherapy, radiotherapy or surgery); or other antibodies (including but not limited to VEGF, EGFR, Her2/neu, VEGF receptors, other growth factor receptors, CD20, CD40, CTLA-4, OX-40, 4-IBB, and ICOS).

In another aspect, the present invention is directed to a composition containing the antibody or an antigen-binding fragment thereof for administration in combination with a PD-1 antibody or a PD-L1 antibody. In another aspect of the present invention, provided is a method of preventing or treating a tumor or a cancer including administering the antibody or an antigen-binding fragment thereof in combination with a PD-1 antibody or a PD-L1 antibody to a patient with a tumor or a cancer. In another aspect of the present invention, provided are the use of the antibody or antigen-binding fragment thereof for administration in combination with a PD-1 antibody or a PD-L1 antibody to treat a tumor or a cancer.

The antibody or antigen-binding fragment thereof may be administered simultaneously with a PD-1 antibody or a PD-L1 antibody, or may be administered separately therefrom with a time interval therebetween. The separate administration of the PD-1 antibody or PD-L1 antibody may be performed before or after administration of the antibody or antigen-binding fragment thereof.

Since the composition uses the anti-VISTA antibody or an antigen-binding fragment thereof according to the present invention as an active ingredient, descriptions in common therebetween are omitted.

The pharmaceutically acceptable carrier contained in the pharmaceutical composition may include a pharmaceutically acceptable carrier commonly used in preparations, and may include, but without being limited to, lactose, dextrose, sucrose, sorbitol, mannitol, starch, gum acacia, calcium phosphate, alginate, gelatin, calcium silicate, microcrystalline cellulose, polyvinylpyrrolidone, water, syrup, methylcellulose, methylhydroxybenzoate, propylhydroxybenzoate, talc, magnesium stearate, mineral oil and the like. The composition according to the present invention may further contain a lubricant, a wetting agent, a sweetener, a flavoring agent, an emulsifier, a suspension agent, a preservative, or the like, in addition to the ingredients described above.

The pharmaceutical composition according to the present invention may be administered orally or parenterally. The parenteral administration may be intravenous injection, subcutaneous injection, intramuscular injection, intraperitoneal injection, endothelial administration, topical administration, intranasal administration, pulmonary administration, rectal administration or the like.

Upon oral administration, since proteins or peptides are digested, an oral composition should be coated with an active drug or formulated so as to protect the same from degradation in the stomach. In addition, the pharmaceutical composition may be administered using any device capable of delivering the active substance to target cells.

The suitable dose of the pharmaceutical composition according to the present invention may vary depending on factors such as the formulation method, administration method, and age, body weight, gender, pathological conditions, diet, administration time, administration route, excretion rate and responsiveness of the patient, and a general physician of ordinary skill can easily determine and prescribe a dose effective for the desired treatment or prevention. For example, the daily dose of the pharmaceutical composition according to the present invention may be within the range of 0.001 to 100 mg/kg. The term "pharmaceutically effective amount" may mean an amount sufficient to prevent or treat a cancer or autoimmune disease.

The pharmaceutical composition according to the present invention may be prepared into a unit dose form, or may be incorporated into a multi-dose container through formulation using a pharmaceutically acceptable carrier and/or excipient according to a method that can be easily implemented by those skilled in the art to which the present invention pertains. In this case, the formulation may be in the form of a solution, a suspension, a syrup or an emulsion in an oil or aqueous medium, or may be in the form of an extract, a powder, a granule, a tablet or a capsule. The composition may further contain a dispersant or a stabilizer.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1. Screening of Antibodies Binding to VISTA

Human naive ScFv (scFv) libraries disclosed in Korean Patent Laid-Open No. 10-2008-0109417 were used for antibody libraries for screening antibodies binding to VISTA and preparation of the libraries. 100 µl of an antigen (hVISTA-Fc, R&D systems. Cat. No. 7126-B7) was plated at 2 µl/ml onto a 96-well immunoplate and incubated for 4° C. overnight. The next day, the antigen-coated plate was washed three times with PBS, and was then reacted with 200 µl of 2% BSA blocking buffer at room temperature for 2 hours. 50 µl of XL1-Blue stock was added to 2 ml of 2× YT-TET (tetracycline 10 µg/ml) growth medium and incubated at 37° C. for 2 hours at 200 rpm, and 13 ml thereof was further added and incubated until $OD_{600}$ reached 0.5. After blocking for 2 hours, the well was washed 3 times with 1×PBS. The phage library group was combined with each washed well, and the phage library and 4% BSA were mixed in equal amounts, and then 200 µl of the mixture was added thereto, followed by rocking at room temperature for 30 minutes and allowing a reaction to proceed for 2 hours. After the phage library reaction was completed, the supernatant was discarded, the residue was washed 5 times with 0.05% PBST and washed 5 times with PBS, 100 µl of 100 mM TEA (trimethylamine) was added to each well, and the resulting mixture was shaken at room temperature for 10 minutes. After 10 minutes, 50 µl of 1 M Tris (pH 7.5) was added to each well, followed by mixing. The supernatant was added to 10 ml of XL1-blue having $OD_{600}$ of 0.5 to conduct infection at 37° C. for 30 minutes. After the infection was completed, 100 µl was used as an output titer and the residue was centrifuged at 7,000 rpm for 10 minutes. The supernatant was discarded and the precipitate was spread over a large square plate (CM 34 µg/ml+1% glucose) and incubated at 30° C. overnight. The 100 µl left as an output titer was diluted to 1/10, 1/100, and 1/1000, spread on a CM plate and incubated overnight at 37° C. The next day, colonies grown on the square plate were scraped using a loop after the addition of 50 ml of 2× YT medium thereto and centrifuged at 7,000 rpm for 10 minutes, the supernatant was discarded, and the precipitate was used to prepare a primary panning stock. 100 ml of a 2× YT culture medium (growth medium: CM 34 µg/ml+1% glucose) was placed in a 500 ml Erlenmeyer flask, cells were added thereto to adjust the $OD_{600}$ to 0.2 and were grown at 200 rpm and 37° C. to adjust the $OD_{600}$ to 0.5. After the cells were cultured until the $OD_{600}$ reached 0.5, a helper phage (M13KO7 mutant) was added in an amount 20 times that of the cells. After infection with the helper phage at 37° C. for 30 minutes, centrifugation was performed at 7,000 rpm for 10 minutes. The supernatant was discarded and the cells were incubated overnight in 100 ml of a fresh 2×YT medium (CM 34 µg/ml+Kan. 70 µg/ml+1 mM IPTG+5 mM $MgCl_2$) at 200 rpm and 30° C. The next day, the grown cells were centrifuged at 7,000 rpm for 10 minutes and centrifuged once more in the same manner as above. The collected supernatant was precipitated on ice in the presence of 1/5 (v/v) 20% PEG/2.5 m NaCl of the supernatant for 1 hour. After precipitation, centrifugation was performed at 7,000 rpm for 1 hour. The supernatant was discarded, and the precipitate was released with 3 ml of PBS, filtered through a 0.45 µm filter, stored at 4° C., and used in the next panning process. This process was repeated 3 to 4 times, and the antibody binding to the antigen was identified through ELISA.

Example 2. Monoclonal ScFv Phage ELISA

After the panning process was completed, the final round cell stock was diluted to form 200 to 500 colonies, spread on a CM agar plate, and then incubated overnight at 37° C. The next day, when the colonies grew, 200 µl of 2×YT medium (CM 34 μg/ml+1% glucose) was plated onto a 96-well deep plate, the colony was inserted into each well one by one and the plate was then incubated overnight at 37° C. and 3,000 rpm. The next day, 200 μl of 2×YT medium (CM 34 μg/ml+1% glucose) was plated onto a new 96-well dip plate, and 20 ml of cells grown the day before were injected into each well and grown at 37° C. and 3,000 rpm for 1 hour and 10 minutes. The remaining cells were stored at −70° C. in 100 μl of 50% glycerol. When the cells grew, 1 μl of a helper phage was mixed with 19 μl of 2×YT medium, and 20 μl of the resulting mixture was injected into each well and incubated for 30 minutes at 37° C. After incubation, centrifugation was performed at 3,000 rpm for 10 minutes. The supernatant was discarded and 200 μl of 2×YT medium (CM 34 μg/ml+Kan. 70 μg/ml+1 mM IPTG+5 mM MgCl₂) was added to the residue, followed by incubation in MegaGrow at 30° C. and 3,000 rpm overnight.

1 μg/ml of Ag (hVISTA-Fc, mVISTA-Fc) was plated at 100 μl/well onto a 96-well immunoplate and then incubated overnight at 4° C. The next day, the cells grown the day before were centrifuged at 3,000 rpm for 10 minutes and stored at 4° C. The plated Ag was washed 3 times with 0.05% PBST, and then 200 μl of 2% BSA blocking buffer was added thereto, followed by incubation at 25° C. for 2 hours. After blocking was completed, the result was washed 3 times with 0.05% PBST. 50 μl of 4% BSA was mixed with 50 μl of the phage stored at a down-regulated temperature of 4° C., and reaction therebetween was allowed to proceed while shaking at room temperature for 1 hour. After phage binding was completed, the reaction product was washed three times with 0.05% PBST, 100 μl of HRP-conjugated mouse anti-M13 antibody (1:3000, #GE 27-9421-01) was added thereto, and reaction was allowed to proceed at 25° C. for 1 hour. After the reaction was completed, the resulting product was washed 3 times with 0.05% PBST, 100 μl of TMB (#BD TMB substrate reagent set 555214) was added thereto, color was developed for 3 to 5 minutes, 50 μl of a stop solution was added thereto, and then an assay was performed using an ELISA reader.

TABLE 1

Result of measurement by ELISA to select monoclonal scFv phage binding to VISTA antigen after panning process

| | | Ag: VISTA-FC: | OD |
|---|---|---|---|
| No. | Clone | Human | Mouse |
| 1 | 2B7 | 2.089 | 0.084 |
| 2 | 2C12 | 2.114 | 2.028 |
| 3 | IB8 | 2.135 | 0.302 |
| 4 | 1D10 | 2.058 | 0.228 |
| 8 | 1C9 | 1.871 | 0.079 |
| 9 | 1A12 | 1.875 | 0.080 |
| 13 | 3C5 | 2.201 | 0.106 |

Selected antibodies are shown in Table 2 below.

TABLE 2

| Antibody | | Amino Acid Sequence | SEQ ID NO |
|---|---|---|---|
| 1B8 | Heavy-chain CDR1 | GGSSSNYA | 1 |
| | Heavy-chain CDR2 | IIPIFGTT | 2 |

TABLE 2-continued

| Antibody | | Amino Acid Sequence | SEQ ID NO |
|---|---|---|---|
| | Heavy-chain CDR3 | AKGAIEPWPFYFDN | 3 |
| | Light-chain CDR1 | NSDVGAYNY | 4 |
| | Light-chain CDR2 | DVN | 5 |
| | Light-chain CDR3 | AAWDDSLNGLV | 6 |
| 2C12 | Heavy-chain CDR1 | GYIFTDYY | 7 |
| | Heavy-chain CDR2 | INPYDGRT | 8 |
| | Heavy-chain CDR3 | AKQMGIWDYDAFDI | 9 |
| | Light-chain CDR1 | SSNIGAGYD | 10 |
| | Light-chain CDR2 | GNS | 11 |
| | Light-chain CDR3 | VAWDDSLKAYV | 12 |
| 1A12 | Heavy-chain CDR1 | GFSFHDYT | 13 |
| | Heavy-chain CDR2 | ISWDGTIT | 14 |
| | Heavy-chain CDR3 | AKEDRYDYYSGAFDI | 15 |
| | Light-chain CDR1 | SSDVGGYDY | 16 |
| | Light-chain CDR2 | DVN | 17 |
| | Light-chain CDR3 | SSFAGSNTLRV | 18 |
| 3C5 | Heavy-chain CDR1 | GYTFSSYW | 19 |
| | Heavy-chain CDR2 | INPGNGHT | 20 |
| | Heavy-chain CDR3 | AKDIAYYDFWSGDAFDL | 21 |
| | Light-chain CDR1 | KLGNKY | 22 |
| | Light-chain CDR2 | QDN | 23 |
| | Light-chain CDR3 | QTWDRSTGV | 24 |

TABLE 3

| Antibody | | Amino Acid Sequence | SEQ ID NO |
|---|---|---|---|
| 1B8 | VH | QMQLVQSGAEVKKPGSSVKVSCKASGGSSSNY AISWVRQAPGQGLEWMGGIIPIFGTT SYAQKFQGRVTITADSMSTAYMELSSLRSEDTAVYY CAKGAIEPWPFYFDNWGQGTLVTVSS | 25 |
| | VL | QLVLTQPRSVSGSPGQSVTISCTGTNSDVGAYNY LSWYQQLPGRAPKVIIYDVN KRPSGVPDRFSGSRSGKTASLTISGLQAEDEADYYC AAWDDSLNGLVFGGGTKLTVLG | 26 |
| 2C12 | VH | QVQLVESGAEVKKPGASVKVSCKASGYIFTDYY MHWVRQAPGQGLEWMGVINPYDGRT SFAQKFQGRLTVTRDTSTSTAYMDLSGLRSEDTAVYY C AKQMGIWDYDAFDIWGQGTMVTVSS | 27 |
| | VL | QFVLTQPSSVSGAPGQRVIISCTGSSSNIGAGYC VHWYQQLPGTAPKVLIYGNS DRPSGVPDRFSASKSATSASLAITGLQAEDEADYYC VAWDDSLKAYVFGTGTKVTVLG | 28 |

TABLE 3-continued

| Anti-body | | Amino Acid Sequence | SEQ ID NO |
|---|---|---|---|
| 1A12 | VH | QMQLESGGGLVEPGRSLRLSCTTSGFSFHDYT MYWVRQVPGKGLEWVSLISWDGTIT FYADPVRGRFTISRDNSKNSLYLQMNSLRAEDTAVYY C AKEDRYDYYSGAFDIWGQGTVVTVSS | 29 |
| | VL | QSALTQPRSVSGSPGQSVTISCTGTSSDVGGYDY VSWYQQHPGKAPKLILNDVN KRPSGVPDRFSGSKSGNTASLTISGLQPPDEADYYC SSFAGSNTLRVFGGGTKLTVLG | 30 |
| 3C5 | VH | QVQLVQSGAEVKKPGASVKLSCKASGYTFSSYW MHWVRQAPGQRLEWMGEINPGNGHT NYEKFKSRVTITDKSASTAYMELSSLRSEDTAVYYC AKDIAYYDFWSGDAFDLWGQGTMVTVSS | 31 |
| | VL | SYELTQPLSVSVSPGQTASITCSGDKLGNKY ASWYQQKPGQSPVLVIYQDN KRPSGIPERFSGSNSGNTATLTISGTQATDEADYYC QTWDRSTGVFGTGTKVTVLG | 32 |

Example 3. Binding of Anti-VISTA ScFV Phage to VISTA Expressing CHO-K1 Cells

CHO-K1 cells expressing human VISTA and mouse VISTA were produced in order to determine whether or not the screened antibody binds to cells expressing VISTA. 50 µl of the produced cells were plated onto a 96-well dip plate at a density of $4 \times 10^6$ cells/ml in FACS buffer (2% FBS, 0.05% sodium azide in PBS), 50 µl of phage supernatant undergoing phage incubation was added thereto, and was incubated at room temperature for 1 hour. After incubation, 400 µl of FACS buffer was added to each well, followed by centrifugation at 2,000 rpm for 5 minutes. The supernatant was discarded and 100 µl of anti-M13 antibody (1:1000) was added to the residue, followed by reaction at 4° C. for 1 hour. After the reaction was completed, 400 µl of FACS buffer was added to each well, followed by centrifugation at 2,000 rpm for 5 minutes. The supernatant was discarded, and 100 µl of anti-mouse IgG-PE antibody (1:500) was added thereto, followed by reaction at 4° C. for 1 hour. After the reaction was completed, 400 µl of FACS buffer was added to each well, followed by centrifugation at 2,000 rpm for 5 minutes. The supernatant was discarded, and 200 µl of FACS buffer was added thereto, followed by assay using FACS (Beckton Dickinson, FACSCalibur). The results are shown in FIG. 1.

As can be seen from FIG. 1, all of the selected antibodies bound to the CHO-K1 cells produced to overexpress human VISTA. The 6A6 used as a negative control group did not bind thereto and the VISTA antibody (R&D systems #FAB71261A) used as a positive control group bound to cells well, as expected.

Example 4. Anti-VISTA IgG Expression

Conversion of the screened scFv phage to the IgG form was performed using molecular biology techniques. Phagemid was extracted from the screened E. Coli clone and double-cut with restriction enzyme Sfi I (R0123, New England Biolabs, US) to obtain a heavy-chain variable-region DNA fragment, and a pIgGHD-6A6Hvy vector including a heavy-chain constant region was treated with Sfi I, and the variable-region DNA fragment was then inserted. In the same manner as above, the phagemid was double-cut with the restriction enzyme BstX I (R0113, New England Biolabs) to obtain a light-chain variable region DNA fragment, a pIgGLD-6A6Lgt vector including a light-chain constant region was double-cut with BstX I, and the variable-region DNA fragment was inserted to complete DNA cloning into an IgG form.

The transient expression of IgG was performed using an Expi293F expression system kit (Thermo Fisher Scientific, US). Expi293 cells included in the kit were subjected to suspension culture on a 125 rpm orbital shaker at 37° C. and 5% $CO_2$ using a dedicated medium. Every 3 days, the cells were passage-cultured to $3 \times 10^3$ cells/ml, and when an expression vector was introduced, the number of cells was adjusted to $3 \times 10^6$ cells/ml before use. The gene introduction was performed using, as a dedicated reagent, Expi-Fectamine, and a Lipid-DNA complex containing 1 µg of an expression vector DNA and 2.7 µl of ExpiFectamine per 1 ml of a cell suspension was prepared and added to the cell suspension. 16 to 18 hours after the introduction, the half (½) of an enhancer was added to induce expression. Then, the cells were cultured under the same conditions as above for 3 to 4 days and centrifuged to obtain a supernatant containing IgG.

Example 5. Purification of Anti-PD-L1 Antibody

The obtained supernatant was injected into a protein A column (GE Healthcare) and IgG was purified through affinity chromatography. After the column was equilibrated with 20 mM Tris-HCl, 50 mM NaCl, and 5 mM EDTA (pH 7.0), the supernatant was injected, washed with 50 mM Tris-HCl, 500 mM NaCl, 5 mM EDTA, and 0.2% polysorbate 20 (pH 7.0) solution, eluted with 50 mM NaCl, 0.1 M glycine-HCl (pH 3.5) and neutralized with 1 M Tris. The eluted protein was dialyzed using MWCO 10,000 spectra/por dialysis membrane (Spectrum Labs, US) to replace the solvent with PBS. Then, the protein was concentrated to the required concentration using Vivaspin (Sartorius, Del.), dispensed and stored at −80° C.

After purification, each antibody was treated with non-reducing and reducing LDS sample buffers (Thermo Fisher Scientific) and electrophoresed using a NuPAGE System (Thermo Fisher Scientific). As a result, IgG having a total molecular weight of about 150 kDa including a 50 kDa heavy chain and a 25 kDa light chain was obtained.

Example 6. Binding Ability of Anti-VISTA Antibody to Antigen

The binding ability of the screened antibody to the antigen was measured using an Octet (ForteBio). For this purpose, the antibody was immobilized on a biosensor, various concentrations of antigen were added to a 96-well plate, and then the binding ability was measured.

TABLE 4

Results of determination of binding ability of various concentrations of anti-VISTA antibody to VISTA antigen in order to measure binding ability therebetween

| | kon(1/Ms) | kdis(1/s) | KD (M) |
|---|---|---|---|
| #2B7 | 2.45E+04 | 1.42E−04 | 5.80E−09 |
| #2C12(H) | 8.34E+04 | 8.48E−05 | 1.02E−09 |
| #2C12(M) | 5.57E+04 | 7.80E−04 | 1.40E−08 |
| #1B8 | 1.11E+05 | 1.03E−03 | 9.29E−09 |

TABLE 4-continued

Results of determination of binding ability
of various concentrations of anti-VISTA antibody to VISTA
antigen in order to measure binding ability therebetween

|       | kon(1/Ms) | kdis(1/s) | KD (M)    |
|-------|-----------|-----------|-----------|
| #1D10 | 4.17E+04  | 1.81E−04  | 4.34E−09  |
| #1C9  | 2.33E+05  | 7.30E−04  | 3.13E−09  |
| #1A12 | 5.02E+04  | 2.74E−05  | 5.46E−10  |
| #3C5  | 2.64E+05  | 3.67E−03  | 1.39E−08  |

Example 7. Cross-Reactivity of Anti-VISTA Antibody to Human and Mouse VISTA

ELISA assay: 1 μg/ml of Ag (human VISTA-Fc or mouse VISTA-Fc) was plated at 100 μl/well onto a 96-well plate and incubated at 4° C. overnight. The next day, the plated Ag was washed 3 times with 0.05% PBST and 200 μl of 2% BSA blocking buffer was added thereto, followed by incubation at 25° C. for 2 hours. After blocking was completed, the resulting product was washed 3 times with 0.05% PBST. 1 μg/ml of each antibody was injected at 100 μl/well and incubated at 25° C. for 1 hour. After incubation was completed, the resulting product was washed 3 times with 0.05% PBST and 100 μl of goat anti-human IgG (kappa)-conjugated peroxidase (1:2000, Bethyl Lab #A80-115P) was added thereto, followed by incubation at 25° C. for minutes. After incubation, the resulting product was washed 3 times with 0.05% PBST, 100 μl of TMB (BD TMB substrate reagent set #555214) was added, color was developed for 3 to 5 minutes, 50 μl of a stop solution was added thereto, and then an assay was performed using an ELISA reader. The results are shown in FIG. 2.

As shown in FIG. 2, all of the screened antibodies bound to human VISTA, in particular, the 2C12 antibody bound well to mouse VISTA as well as human VISTA.

FACS assay: to identify overexpression of human and mouse VISTA in CHO-K1 cells, a cell solution ($5 \times 10^5$ cells/100 μl/FACS tube) at a concentration of $5 \times 10^6$/ml in FACS buffer (2% FBS, 0.05% sodium azide in PBS) was prepared, 2 μg/ml of the screened antibody was prepared, and 100 μl of the cell solution and 100 μl of the antibody were placed in a FACS tube and then incubated at 4° C. for 30 minutes. After incubation was completed, 2 ml of FACS buffer was added to each tube, followed by centrifugation at 1,500 rpm for 5 minutes. The supernatant was discarded, 100 μl of a goat anti-human IgG-Fc-conjugated PE (A80-248PE, 1:500) was added to each tube, and a reaction was allowed to proceed at 4° C. for 20 minutes. In the case of a positive control group, 5 μl of APC-conjugated anti-hVISTA (R&D #71261A) was added to hVISTA over-expressing cells (in the same amount as sample) and in the case of mice, 1 μl of APC-conjugated anti-mVISTA (BioLegend #143710) was added to mVISTA over-expressing cells (in the same amount as the sample), followed by reaction at 4° C. for 20 minutes. When the reaction was completed, 2 ml of FACS buffer was added to each well, followed by centrifugation at 1,500 rpm for 5 minutes. The supernatant was discarded, and 200 μl of FACS buffer was added thereto, followed by an assay using BD FACSCalibur. The results are shown in FIG. 3.

As shown in FIG. 3, when treating CHO-K1 cells prepared to overexpress VISTA with the screened anti-VISTA, like in ELISA, all screened antibodies bound to CHO-K1 expressing human VISTA on the surface thereof and the 2C12 antibody also bound to CHO-K1 expressing mouse VISTA on the surface thereof.

Example 8. Allo-MLR Assay of Anti-VISTA Antibody 50 ml of human peripheral blood was collected from a donor and diluted 3-fold with PBS containing 2 mM EDTA. 15 ml of Ficoll-Paque (GE #17-1440-03) was injected into a fresh 50 ml tube, and 30 ml of diluted blood was slowly loaded, followed by centrifugation at 2,000 rpm for 40 minutes. The PBMC layer was recovered, transferred to a 50 ml tube and washed with washing buffer (RPMI1640 medium containing 2% FBS and 10 mM HEPES) by centrifugation at 1,600 rpm for 10 minutes. After centrifugation, the supernatant was discarded and washed repeatedly. The cell pellets left after centrifugation were released into single cells with 50 ml of washing buffer, and then a dead cell mass was removed using a cell strainer (40 um). The cells (donor A or B) to be used as responders of Allo-MLR were diluted to a concentration of $4 \times 10^6$ cells/ml with MLR medium (RPMI1640 medium containing 10% FBS, 10 mM HEPES, 1 mM pyruvate, NEAA (100×), 2 mM L-glutamine, 1% antibiotics, $10^{-5}$ M β-ME). Cells (donor B or A) to be used as stimulators were treated with mitomycin C (MMC) to inhibit cell proliferation. The method will be described in detail as follows. Cells to be used as stimulators were diluted in MLR medium at a concentration of $4 \times 10^6$ cells/ml in a 50 ml tube, and MMC was added to reach a total volume of 25 μg/ml, followed by reaction for 30 minutes at 37° C. After the reaction was completed, a 50 ml tube was completely filled with a washing buffer and centrifugation was performed at 1,200 rpm for 10 minutes, followed by washing. This process was performed 4 times to completely remove MMC. Finally, the residue was diluted in MLR medium to a concentration of $4 \times 10^6$ cells/ml. The prepared cells were aliquoted at $2 \times 10^3$ cells/well (50 μl) into a 96-well cell culture plate. 50 μl of the antibody to be analyzed was added to realize final concentrations of 30 μg/ml and 10 μg/ml. The antibody was tested using 3 wells for each concentration. After incubation for 5 days in a CO$_2$ incubator at 37° C., 50 μl of the cell culture supernatant was stored separately for measuring IFN-γ production, and the remaining cells were used for analysis of cell proliferation. The cell proliferation was analyzed by measuring the amount of ATP produced in cells left after allo-MLR. The method is described in detail as follows. 100 μl (equivalent to cell culture solution) of CellTiter-Glo® Luminescent cell viability assay (Promega) solution was added to the cultured cells and reacted for 10 minutes at room temperature to induce lysis of the cells. Cell viability was measured using a luminometer. The results are shown in FIG. 4.

As shown in FIG. 4, the competitors (positive control group) and 1B8 clones induced expression of more interferon-gamma than the group treated with non-specific antibody (whole IgG), and all other clones induced lower interferon-gamma expression than whole IgG. In other words, these clones are clones that suppress the expression of interferon-gamma. Among them, 2C12, 1A12 and 3C5 exhibited excellent interferon-gamma expression suppression ability.

Example 9. Anti-Tumor Activity of Anti-VISTA Antibody

The anticancer efficacy of caudal vein administration of human PBMCs and JNJ61610588, pembrolizumab and anti- VISTA mAb 1B8 therapeutic agents was determined using NSG mice including pads transplanted with a human-derived breast cancer cell line, MDA-MB-231 mammary fat, to evaluate the anti-tumor activity of the anti-VISTA antibody. The experiment was conducted jointly with Laboratory Animal Resource Center, the Korea Research Institute of Bioscience and Biotechnology.

The human breast cancer cell line, MDA-MB-231, was thawed and cultured in a $CO_2$ incubator (Forma, USA) at a temperature of 37° C. and a $CO_2$ concentration of 5%. On the final day of culture, all cancer cells were collected and counted, and the cell concentration was adjusted to $3\times10^7$ cells/ml using serum-free media. The cell culture solution thus adjusted was injected at 0.1 ml ($3\times10^6$ cells/mouse) into each of left and right regions of the mouse breast fat pad.

After transplantation with the cancer cells, when the average tumor size for each group reached 46.9 mm$^3$, PBMC ($4\times10^7$ cells/ml) of A type (No. 1 mouse in each group), B type (No. 2 mouse in each group), C type (No. 3 mouse in each group), D type (No. 4 mouse in each group), E type (No. 5 mouse in each group) and F type (No. 6 mouse in each group) was injected at 0.16 ml ($0.64\times10^7$ cells/mouse) through caudal vein administration.

For PBMC separation, 50 ml of human peripheral blood was collected from a donor and diluted 3-fold with PBS containing 2 mM EDTA. 15 ml of Ficoll-Paque (GE #17-1440-03) was injected into a fresh 50 ml tube, and 30 ml of diluted blood was slowly loaded therein, followed by centrifugation at 2,000 rpm for 40 minutes. The PBMC layer was recovered and transferred to a 50 ml tube, and the cells were washed with a washing buffer (RPMI1640 medium containing 2% FBS and 10 mM HEPES) by centrifugation at 1,600 rpm for 10 minutes. After centrifugation, the supernatant was discarded and washed four times. The cell pellets left after centrifugation were released into single cells with 50 ml of washing buffer, and were then diluted to a concentration of $2\times10^7$ cells/mL in PBS medium.

For the organization of the mouse group and administration of drug into the mouse group, after PBMC injection, drug administration was started. The drug was administered through the caudal vein at 5 mg/kg into each group of Group 1: PBMC+human whole IgG (control); Group 2: PBMC+competitor (JNJ 61610588); Group 3: PBMC+pembrolizumab; Group 4: PBMC+anti VISTA mAb(1B8); and Group 5: PBMC+pembrolizumab+anti VISTA mAb(1B8).

After PBMC injection, the drug was first administered at 0.2 ml per mouse twice a week for a total of 7 times.

All animals were observed for general clinical symptoms and changes in body weight and tumor size at the beginning of administration and immediately before each administration during the experimental period.

The change in tumor size was expressed using the formula length×width×height/2 after measuring left and right tumors in three directions using a Vernier caliper for each of 12 subjects from the time at which the average tumor size of each cancer cell transplant group reached 46.9 mm$^3$ until the $25^{th}$ day thereafter.

On the $25^{th}$ day from the beginning of drug administration, 3 healthy mice per group were selected, blood was collected from the orbital veins thereof (EDTA tube), the mice were sacrificed using $CO_2$ gas, the spleen was extracted and immobilized in PBS, and the tumors were divided into right and left sections. The tumors were weighed using a chemical balance and then imaged and immobilized in liquid nitrogen and formalin.

As a result, no administration groups exhibited specific general symptoms during the test period, but the solvent control group (PBMC+PBS) No. 2 mouse and the PBMC+Anti-VISTA mAb 1B8 administration group No. 5 mouse showed weight loss from the $17^{th}$ day and the $21^{th}$ day, respectively, to the last day, compared to the initial weight thereof (Table 5 and FIG. 5).

TABLE 5

Weight change of mouse on each day (%)

| Group (n = 6) | Dose (mg/kg) | Day 0 | 3 | 5 | 7 | 10 | 12 | 14 | 17 | 19 | 21 | 24 | 25 |
|---|---|---|---|---|---|---|---|---|---|---|---|---|---|
| PBMC + PBS (Solvent control group) | 0 | 100.0 ± 0.0 | 103.4 ± 0.3 | 104.7 ± 0.5 | 107.7 ± 1.3 | 110.4 ± 2.7 | 112.2 ± 2.5 | 115.5 ± 4.2 | 117.3 ± 6.0 | 118.9 ± 6.9 | 120.0 ± 8.6 | 120.6 ± 11.5 | 122.0 ± 13.1 |
| PBMC + JNJ6161058B | 5 | 100.0 ± 0.0 | 102.0 ± 1.3 | 104.1 ± 1.6 | 106.6 ± 2.4 | 109.6 ± 4.0 | 112.0 ± 4.0 | 113.6 ± 3.9 | 116.6 ± 3.4 | 118.4 ± 3.7 | 121.5 ± 3.3 | 126.6 ± 4.1 | 128.8 ± 3.7 |
| PBMC + Pembrolizumab | 5 | 100.0 ± 0.0 | 101.5 ± 1.9 | 103.6 ± 2.5 | 106.1 ± 2.1 | 108.9 ± 3.0 | 111.4 ± 2.8 | 112.8 ± 4.1 | 114.4 ± 3.6 | 113.1 ± 4.6 | 114.3 ± 5.3 | 114.5 ± 6.9 | 118.2 ± 5.3 |
| PBMC + Anti-VISTA mAb 1B8 | 5 | 100.0 ± 0.0 | 101.7 ± 1.1 | 103.7 ± 1.4 | 107.2 ± 2.2 | 109.7 ± 2.5 | 113.2 ± 2.4 | 114.5 ± 3.6 | 118.2 ± 5.0 | 120.6 ± 5.2 | 122.1 ± 6.5 | 123.6 ± 11.9 | 125.4 ± 13.6 |
| PBMC + Pbrlzm + Anti-VI mAb 1B8 | 5 + 5 | 100.0 ± 0.0 | 101.2 ± 1.5 | 103.3 ± 1.7 | 105.8 ± 1.9 | 108.6 ± 2.1 | 110.0 ± 2.0 | 112.3 ± 1.9 | 114.2 ± 3.2 | 113.6 ± 3.1 | 115.5 ± 3.5 | 117.4 ± 4.3 | 119.9 ± 3.5 |

On the $25^{th}$ day after the beginning of drug administration, the MDA-MB-231 tumor was excised and weighed. As a result, PBMC+JNJ61610588 (5 mg/kg), PBMC+pembrolizumab (5 mg/kg), PBMC+Anti-VISTA mAb 1B8 (5 mg/kg) and PBMC+Pembrolizumab+Anti-VISTA mAb (5+5 mg/kg) administration groups exhibited statistically significant reductions in tumor weight of 18.9% (p<0.05), 32.9% (p<0.001), 37.8% (p<0.001) and 60.6% (p<0.001), respectively (Table 6, FIG. 6), compared to the solvent control group (PBMC+human whole IgG).

TABLE 6

Change in tumor size and tumor weight on last day

| Group (n = 6, Left + right) | Dose (mg/kg) | Tumor volume (Vt-Vo)† Day | | | | | |
|---|---|---|---|---|---|---|---|
| | | 0 | 3 | 5 | 7 | 10 | 12 | 14 |
| PBMC + PBS (Solvent Control Group) | 0 | 0.0 ± 0.0 | 16.5 ± 2.6 | 36.8 ± 10.2 | 67.2 ± 15.1 | 128.5 ± 22.9 | 225.5 ± 35.4 | 317.3 ± 51.1 |
| PBMC + JNJ61610588 | 5 | 0.0 ± 0.0 | 12.1 ± 5.3* 26.5% ‡ | 26.2 ± 9.0* 28.9% | 49.8 ± 18.5* 25.9% | 94.6 ± 27.2** 26.4% | 163.2 ± 57.3** 27.6% | 239.7 ± 79.6** 24.5% |
| PBMC + Pembrolizumab | 5 | 0.0 ± 0.0 | 13.4 ± 1.8** 18.9% | 30.3 ± 5.6 17.8% | 55.2 ± 11.0* 17.8% | 105.7 ± 18.1* 17.8% | 181.5 ± 37.3** 19.5% | 249.3 ± 50.3** 21.4% |
| PBMC + Anti-VISTA mAb 1B8 | 5 | 0.0 ± 0.0 | 13.6 ± 3.2* 18.0% | 27.6 ± 6.5* 25.0% | 49.9 ± 11.5** 25.7% | 93.9 ± 21.6*** 26.9% | 164.3 ± 35.3*** 27.2% | 225.4 ± 53.6*** 29.0% |
| PBMC + Pbrlzm + Anti-VI mAb 1B8 | 5 | 0.0 ± 0.0 | 10.6 ± 3.0*** 35.6% | 22.9 ± 6.3*** 37.7% | 42.0 ± 14.3*** 37.5% | 78.8 ± 18.1*** 38.7% | 128.1 ± 31.7*** 43.2% | 153.1 ± 42.5*** 51.8% |

| Group (n = 6, Left + right) | Dose (mg/kg) | Tumor volume (Vt-Vo)† Day | | | | | Tumor weight (mg) |
|---|---|---|---|---|---|---|---|
| | | 17 | 19 | 21 | 24 | 25 | 25 |
| PBMC + PBS (Solvent Control Group) | 0 | 440.4 ± 71.0 | 572.4 ± 96.5 | 688.4 ± 107.5 | 837.8 ± 146.5 | 964.0 ± 158.2 | 1110.5 ± 172.4 |
| PBMC + JNJ61610588 | 5 | 330.2 ± 88.6** 25.0% | 429.8 ± 104.7** 24.9% | 526.1 ± 115.9** 23.6% | 668.0 ± 155.0* 20.3% | 782.5 ± 218.9* 18.8% | 900.8 ± 247.9* 18.9% |
| PBMC + Pembrolizumab | 5 | 311.9 ± 56.4*** 29.2% | 392.8 ± 73.2*** 31.4% | 473.2 ± 74.2*** 31.3% | 568.5 ± 84.2*** 32.1% | 656.2 ± 141.2*** 31.9% | 744.9 ± 163.0*** 32.9% |
| PBMC + Anti-VISTA mAb 1B8 | 5 | 278.3 ± 66.3*** 36.8% | 353.7 ± 87.0*** 38.2% | 424.5 ± 96.6*** 38.3% | 527.5 ± 115.7*** 37.0% | 599.4 ± 173.8*** 37.8% | 691.2 ± 209.1*** 37.8% |
| PBMC + Pbrlzm + Anti-VI mAb 1B8 | 5 | 184.9 ± 49.0*** 58.0% | 232.2 ± 58.8*** 59.4% | 276.7 ± 69.6*** 59.8% | 340.6 ± 80.6*** 59.3% | 378.5 ± 95.0*** 60.7% | 437.8 ± 98.1*** 60.6% |

Example 10. Production and Screening of Variants to Enhance Affinity

Antibody optimization was performed to enhance the affinity of the anti-VISTA antibody clone 1B8. A primer having random mutations introduced into the light-chain CDR3 and heavy-chain CDR3 of 1B8 was produced using a soft-randomization method that preserves 80% of the original DNA sequence of 1B8 and randomizes the same. A DNA fragment encoding a light-chain variable region of 1B8 and a heavy-chain variable region of ME4 into which a mutation was introduced was obtained through PCR using the primer. Each of the light-chain variable region and the heavy-chain variable region of the 1B8 scFv phage phagemid was replaced with the DNA fragment to produce a 1B8 light-chain CDR3 variant scFv phage library and a heavy-chain CDR3 variant scFv phage DNA library, respectively.

The variant scFv phage DNA library was purified using phenol-chloroform and then transformed into an *E. coli* strain, XL-1 Blue, using electroporation. Diversity acquisition was identified through transformation efficiency analysis and DNA sequence analysis, phage expression was induced by culturing at a 500 ml scale, and a 1B8 light-chain CDR3 variant scFv phage library was produced using a PEG-precipitation method.

Biopanning was performed using each variant scFv phage library in the same manner as in Example 1. Then, in the screening process, the dissociation rate constant (kdis) of scFv was measured as a quantitative index for evaluating the binding retention ability. The result showed that 7 screened optimized clones retained the heavy-chain variable region of 1B8. The result of measurement of the dissociation rate constants (Table 7) and the amino acid sequence (Tables 8 and 9) of the 7 screened optimized clones are shown.

The result of measurement of dissociation rate constants of the seven optimized anti-VISTA antibodies showed that the PMC-309.3.3 sequence was obtained by substituting N (Aps) of the CDR3 portion of the best anti-VISTA.H2 with Y (Tyr). The result of comparison and analysis of the sequence of PMC-309.3.3 with a human germline base sequence using IMGT software showed that the heavy-chain variable region was derived from IGHV1-69*06. The result of comparison with the amino acid sequence of IGHV1-69*06 of the germline group showed that 4 amino acid residues of the framework region (FR) were substituted. In order to increase the folding efficiency while maintaining antigen-binding ability, PMC 309.3.4 with increased efficiency through substitution of the FR portion was produced. The specific sequence of PMC 309.3.4 is as shown in Table 10.

TABLE 7

| Phage clone | Kdis(1/s) |
|---|---|
| Anti VISTA.3.0 (1B8) | 7.32E-04 |
| Anti VISTA_B5 | 6.16E-04 |
| Anti VISTA_G1 | 5.74E-04 |
| Anti VISTA_H2 (1) | 2.85E-04 |
| Anti VISTA_V3_1 | 4.87E-04 |

TABLE 7-continued

| Phage clone | Kdis(1/s) |
|---|---|
| Anti VISTA_V3_2 | 1.08E-03 |
| Anti VISTA_V3_3 | 1.27E-03 |
| Anti VISTA_V3_4 | 2.22E-03 |

TABLE 8

| | | Amino acid sequence | SEQ ID No.: |
|---|---|---|---|
| Anti VISTA_B5 | VL_CDR3 | AAWDDDLNGLV | 33 |
| Anti VISTA_G1 | VL_CDR3 | AAWDDSLIGHV | 34 |
| Anti VISTA_H2 | VL_CDR3 | AAWDDNLNGLV | 35 |
| Anti VISTA_V3_1 | VL_CDR3 | AAWDDSLYGLV | 36 |
| Anti VISTA_V3_2 | VL_CDR3 | AAWDDSLNDLV | 37 |
| Anti VISTA_V3_3 | VL_CDR3 | AAWDDSLNVLV | 38 |
| Anti VISTA_V3_4 | VL_CDR3 | AAWDDNSDFHV | 39 |
| PMC309.3.3 | VL_CDR3 | AAWDDNLYGLV | 40 |

TABLE 9

| Name | Hvy(H1) | Lgt(L2) |
|---|---|---|
| Anti VISTA_B5 | QMQLVQSGAEVKKPGSSV KVSCKASGGSSSNYAISW VRQAPGQGLEWMGGIIPI FGTTSYAQKFQGRVTITA DGSMSTAYMELSSLRSED TAVYYCAKGAIEPWPFYF DNWGQGTLVTVSS SEQ ID NO.: 25 | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDDL NGLVFGGGTKLTVLG SEQ ID NO.: 41 |
| Anti VISTA_G1 | | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDSL IGHVFGGGTKLTVLG SEQ ID NO.: 42 |
| Anti VISTA_H2 | | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDNL NGLVFGGGTKLTVLG SEQ ID NO.: 43 |
| Anti VISTA_V3_1 | | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDSL YGLVFGGGTKLTVLG SEQ ID NO.: 44 |
| Anti VISTA_V3_2 | | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDSL NDLVFGGGTKLTVLG SEQ ID NO.: 45 |
| Anti VISTA_V3_3 | | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDSL NVLVFGGGTKLTVLG SEQ ID NO.: 46 |
| Anti VISTA_V3_4 | | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDNS DFHVFGGGTKLTVLG SEQ ID NO.: 47 |
| PMC309.3.3 | | QLVLTQPRSVSGSPGQ SVTISCTGTNSDVGAY NYLSWYQQLPGRAPKV HYDVNKRPSGVPDRFG SGRSGKTASLTISGLQ AEDEADYYCAAWDDNL GLVFGGGTKLTVLG SEQ ID NO.: 48 |

TABLE 10

| name | Hvy Lgt | Hvy seq. | Lgt seq. |
|---|---|---|---|
| PMC309.3.4-W | G-H wt Lgt | QVQLVQSGAEVKKP GSSVKYSCKASGGS SSNYAISWVRQAPG QGLEWMGGIIPIFG TTSYAQKFQGRVTI TADKSTSTAYMELS SLRSEGTAVYYCAK GAIEPWPFYFDNWG QGTLVTVSS SEQ ID NO.: 49 | QLVLTQPRSV SGSPGQSVTI SCTGTNSDYG AYNYLSWYQQ LPGRAPKVHY DVNKRPSGVP DRFSGSRSGK TASLTISGLQ AEDEADYYCA AWDDNLYGLV FGGGTKLTVL G SEQ ID NO.: 48 |
| PMC309.3.4-SA | G-H SA | | QSALTQPRSV SGSPGQSVTI SCTGTNSDVG AYNYLSWYQQ LPGRAPKVHY DVNKRPSGYP DRFSGSRSGK TASLTISGLQ AEDEADYYAA WDDNLYGLVV FGGGTKLTVL SEQ ID NO.: 50 |

Example 11. Analysis of Physicochemical Properties of Optimized Anti-VISTA Antibody Each optimized scFv phage clone was converted to an IgG form. Specific DNA cloning, production, and purification methods for the form conversion were performed using the same methods as those described in Examples 4 and 5.

Octet was used to evaluate the binding strength of the optimized anti-VISTA antibody while excluding clones with low productivity therefrom, and the experiment was performed in the same manner as the method presented in Example 6 (Table 11). As can be seen from Table 11, the binding force to human VISTA was significantly increased through the optimization.

TABLE 11

| Ligand | Analyte | KD (M) | kon(1/Ms) | kdis(1/s) | TM Scatter 266 | TM Scatter 473 | TM Ration 350/330 |
|---|---|---|---|---|---|---|---|
| Anti VISTA 3.0(1B8) | VISTA-Fc | 1.36E−08 | 1.54E+055 | 2.09E−03 | 68.98 | 70.93 | 71.03 |
| Anti VISTA_V3_1 | | 2.86E−09 | 5.25E+04 | 1.50E−04 | 70.28 | 71.63 | 74.76 |
| Anti VISTA_V3_2 | | 1.28E−08 | 1.49E+05 | 1.91E−03 | 62.58 | 65.15 | 66.50 |
| PMC-309.3.3 | | 5.16E−10 | 1.85E+05 | 9.56E−05 | 68.53 | 69.26 | 72.10 |
| PMC-309.3.4w | | 4.96E−10 | 1.89E+05 | 9.38E−05 | 69.05 | 70.15 | 78.80 |
| PMC-309.3.4SA | | 6.06E−10 | 2.25E+05 | 1.34E−04 | 62.05 | 66.46 | 67.34 |

Example 12. Allo-MLR Assay of Optimized Anti-VISTA Antibody

In order to evaluate the function of the optimized antibody, a mixed lymphocyte reaction (MLR) was performed in the same manner as in Example 8 to measure the reactivity of immune cells contained in peripheral blood in vitro. Thereby, it was confirmed that cell proliferation and cytokine (IFN-γ) production were induced.

The results are shown in FIGS. 7 and 8. As can be seen from FIGS. 7 and 8, the PMC-309.3.3 drug was very superior to the comparative group and that concentration-dependent cell proliferation and cytokine secretion increased.

Example 13. Anti-Tumor Activity of Optimized Anti-VISTA Antibodies

In order to evaluate the anti-tumor activity of the anti-VISTA antibody, the anticancer efficacy of caudal vein-administered drugs (PMC-309.3.4W, PMC-309.3.45A) having changed light-chain variable regions, including human PBMC and JNJ61610588, PMC-309.3.3, and anti-VISTA 3.4, was evaluated in the same manner as in Example 7 using NSG mice including pads transplanted with a human breast cancer cell line, MDA-MB-231 mammary fat.

As can be seen from Table 12, Table 13, and FIGS. 9 and 10, the result showed that PMC-309.3.3 showed the best anticancer activity, which corresponds to the result in the mixed lymphatic reaction.

TABLE 12

| Group (n = 6) | Dose (mg/kg) | Days after treatment | | | | | | |
|---|---|---|---|---|---|---|---|---|
| | | 0 | 1 | 3 | 6 | 8 | 10 | 13 |
| Solvent control group PBMC + whole IgG | 5 | 100.0 ± 0.0 | 100.5 ± 1.1 | 101.8 ± 0.9 | 104.2 ± 1.6 | 107.0 ± 3.3 | 107.8 ± 3.6 | 109.8 ± 3.8 |
| PBMC + VSTB112 | 5 | 100.0 ± 0.0 | 100.1 ± 1.1 | 101.5 ± 1.6 | 103.8 ± 1.8 | 105.7 ± 2.3 | 106.5 ± 3.2 | 108.3 ± 2.6 |
| PBMC + PMC309.3.3 | 5 | 100.0 ± 0.0 | 100.6 ± 1.2 | 101.6 ± 1.2 | 103.8 ± 1.5 | 105.9 ± 2.3 | 107.3 ± 3.2 | 108.9 ± 3.8 |
| PBMC + PMC3093.4W | 5 | 100.0 ± 0.0 | 99.8 ± 1.1 | 100.9 ± 1.3 | 102.7 ± 1.2 | 104.4 ± 1.4 | 105.0 ± 2.0 | 107.0 ± 2.2 |
| PBMC + PMC309.3.4SA | 5 | 100.0 ± 0.0 | 99.5 ± 1.2 | 100.7 ± 0.8 | 102.7 ± 1.4 | 104.3 ± 2.3 | 104.0 ± 2.5 | 105.9 ± 2.7 |
| Group (n = 6) | Dose (mg/kg) | Days after treatment | | | | | | |
| | | 15 | 17 | 20 | 22 | 24 | 27 | 28 |
| Solvent control group PBMC + whole IgG | 5 | 110.7 ± 4.9 | 111.9 ± 5.9 | 112.7 ± 7.3 | 115.7 ± 5.9 | 117.2 ± 5.4 | 118.5 ± 5.1 | 118.9 ± 5.7 |
| PBMC + VSTB112 | 5 | 109.0 ± 3.4 | 111.2 ± 3.6 | 112.8 ± 4.3 | 114.7 ± 3.9 | 116.5 ± 4.1 | 117.5 ± 5.0 | 118.0 ± 5.3 |
| PBMC + PMC309.3.3 | 5 | 109.5 ± 5.1 | 112.1 ± 4.8 | 114.1 ± 4.5 | 116.5 ± 3.9 | 118.8 ± 4.1 | 120.8 ± 3.7 | 121.3 ± 3.2 |
| PBMC + PMC3093.4W | 5 | 106.6 ± 2.6 | 109.0 ± 1.8 | 110.6 ± 1.9 | 112.7 ± 1.5 | 115.8 ± 2.8 | 118.2 ± 2.7 | 118.3 ± 1.8 |
| PBMC + PMC309.3.4SA | 5 | 105.8 ± 3.0 | 108.1 ± 3.3 | 109.3 ± 3.7 | 111.8 ± 3.8 | 114.2 ± 3.6 | 116.5 ± 4.2 | 117.4 ± 5.2 |

TABLE 13

| Group (n = 6, Left + right) | Dose (mg/kg) | Tumor volume (Vt-Vo)† Day | | | | | |
|---|---|---|---|---|---|---|---|
| | | 0 | 3 | 6 | 8 | 10 | 13 | 15 |

| Group (n = 6, Left + right) | Dose (mg/kg) | 0 | 3 | 6 | 8 | 10 | 13 | 15 |
|---|---|---|---|---|---|---|---|---|
| PBMC + whole IgG (solvent control group) | 0 | 0.0 ± 0.0 | 20.6 ± 4.5 | 56.7 ± 9.7 | 94.8 ± 16.1 | 138.9 ± 21.5 | 256.1 ± 44.4 | 363.5 ± 59.2 |
| PBMC + VSTB112 | 5 | 0.0 ± 0.0 | 14.8 ± 3.5 28.1%‡ | 40.6 ± 8.1 28.4% | 71.6 ± 8.9 24.4% | 105.2 ± 14.5 24.2% | 192.7 ± 27.3 24.7% | 273.3 ± 38.2 24.8% |
| PBMC + PMC309 | 5 | 0.0 ± 0.0 | 11.9 ± 3.6 42.0% | 30.3 ± 7.1 46.5% | 52.1 ± 13.8 45.1% | 73.8 ± 21.3 46.9% | 134.3 ± 29.2* 47.5% | 186.0 ± 48.4*** 48.8% |
| PBMC + PMC309 3.4W | 5 | 0.0 ± 0.0 | 13.0 ± 3.4 36.8% | 33.5 ± 8.0 40.9% | 59.1 ± 16.8 37.6% | 85.4 ± 23.8 38.5% | 157.7 ± 46.8 38.4% | 221.1 ± 63.1** 39.2% |
| PBMC + PMC309 3.4SA | 5 | 0.0 ± 0.0 | 13.4 ± 2.6 34.7% | 33.9 ± 5.4 40.3% | 62.9 ± 12.7 33.7% | 92.5 ± 20.2 33.4% | 169.2 ± 40.7 33.9% | 233.5 ± 42.3* 35.8% |

| Group (n = 6, Left + right) | Dose (mg/kg) | Tumor volume (Vt-Vo)† Day | | | | | Tumor weight (mg) |
|---|---|---|---|---|---|---|---|
| | | 20 | 22 | 24 | 27 | 28 | 28 |
| PBMC + whole (solvent control group) | 0 | 633.4 ± 92.5 | 787.8 ± 103.8 | 996.0 ± 148.2 | 1230.5 ± 173.0 | 1426.5 ± 222.3 | 1509.2 ± 233.6 |
| PBMC + VSTB112 | 5 | 490.3 ± 59.4** 22.6% | 618.6 ± 68.1*** 21.5% | 786.9 ± 80.5*** 21.0% | 980.9 ± 95.6*** 20.3% | 1167.0 ± 179.8*** 18.2% | 1237.6 ± 191.8* 18.0% |
| PBMC + PMC309 | 5 | 314.3 ± 99.3*** 50.4% | 388.4 ± 117.3*** 50.7% | 488.1 ± 444.9*** 51.0% | 602.1 ± 177.5*** 51.1% | 686.8 ± 222.4*** 51.9% | 742.5 ± 224.8*** 50.8% |
| PBMC + PMC309 3.4W | 5 | 381.6 ± 98.8*** 39.7% | 476.9 ± 133.0*** 39.5% | 612.0 ± 157.9*** 38.5% | 769.8 ± 177.7*** 37.4% | 896.3 ± 242.4*** 37.2% | 951.5 ± 244.7*** 37.0% |
| PBMC + PMC309 3.4SA | 5 | 415.6 ± 87.9*** 34.4% | 524.0 ± 121.9*** 33.5% | 663.4 ± 151.3*** 33.4% | 812.1 ± 177.6*** 34.0% | 944.9 ± 198.3*** 33.8% | 1004.3 ± 199.9*** 33.5% |

Significant figures (t-TEST) * p<0.05,  p<0.01, * p<0.001 (vs PBMC+whole IgG)

†Δt=Vt−Vo, Vt(Measurement of the tumor volume), Vo(Initial tumor volume)

‡ Inhibition Rate (vs PBMC+whole IgG)

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

[Sequence Listing Free Text]

An electronic file is attached.

The invention claimed is:

1. An antibody or an antigen-binding fragment thereof binding to V-domain Ig suppressor of T-cell activation (VISTA) comprising:

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5 and a light-chain CDR3 of SEQ ID NO: 6;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 33;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 34;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 35;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 36;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 37;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 38;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 39;

a heavy-chain variable region comprising a heavy-chain CDR1 of SEQ ID NO: 1, a heavy-chain CDR2 of SEQ ID NO: 2 and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 40;

a heavy-chain variable region comprising a heavy-chain CDR1 of SEQ ID NO: 7, a heavy-chain CDR2 of SEQ ID NO: 8 and a heavy-chain CDR3 of SEQ ID NO: 9, and a light-chain variable region comprising a light-chain CDR1 of SEQ ID NO: 10, a light-chain CDR2 of SEQ ID NO: 11, and a light-chain CDR3 of SEQ ID NO: 12;

a heavy-chain variable region comprising a heavy-chain CDR1 of SEQ ID NO: 13, a heavy-chain CDR2 of SEQ ID NO: 14 and a heavy-chain CDR3 of SEQ ID NO: 15, and a light-chain variable region comprising a light-chain CDR1 of SEQ ID NO: 16, a light-chain CDR2 of SEQ ID NO: 17, and a light-chain CDR3 of SEQ ID NO: 18; or a heavy-chain variable region comprising a heavy-chain CDR1 of SEQ ID NO: 19, a heavy-chain CDR2 of SEQ ID NO: 20 and a heavy-chain CDR3 of SEQ ID NO: 21, and a light-chain variable region comprising a light-chain CDR1 of SEQ ID NO: 22, a light-chain CDR2 of SEQ ID NO: 23, and a light-chain CDR3 of SEQ ID NO: 24.

2. The antibody or an antigen-binding fragment thereof according to claim 1, wherein the antibody or an antigen-binding fragment thereof comprises a heavy-chain variable region selected from the group consisting of SEQ ID NOS: 25, 27, 29, 31 and 49.

3. The antibody or an antigen-binding fragment thereof according to claim 1, wherein the antibody or an antigen-binding fragment thereof comprises a light-chain variable region selected from the group consisting of SEQ ID NOS: 26, 28, 30, 32, 41 to 48, and 50.

4. A nucleic acid encoding the antibody or an antigen-binding fragment thereof according to claim 1.

5. An expression vector comprising the nucleic acid according to claim 4.

6. A cell transformed with the expression vector according to claim 5.

7. A method of producing an antibody binding to VISTA or antigen-binding fragment thereof comprising:
   (a) culturing the cell according to claim 6; and
   (b) recovering an antibody or antigen-binding fragment thereof from the cultured cell.

8. A composition comprising the antibody or an antigen-binding fragment thereof according to claim 1.

\* \* \* \* \*

```
                    SEQUENCE LISTING

<160> NUMBER OF SEQ ID NOS: 50

<210> SEQ ID NO 1
<211> LENGTH: 8
<212> TYPE: PRT
<213> ORGANISM: Artificial Sequence
<220> FEATURE:
<223> OTHER INFORMATION: Heavy-chain CDR1

<400> SEQUENCE: 1

Gly Gly Ser Ser Ser Asn Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Heavy-chain CDR2
```

```
<400> SEQUENCE: 2

Ile Ile Pro Ile Phe Gly Thr Thr
1               5

<210> SEQ ID NO 3
<211> LENGTH: 14
<212> TYPE: PRT
<213> ORGANISM: Artificial Sequence
<220> FEATURE:
<223> OTHER INFORMATION: Heavy-chain CDR3

<400> SEQUENCE: 3

Ala Lys Gly Ala Ile Glu Pro Trp Pro Phe Tyr Phe Asp Asn
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Light-chain CDR1

<400> SEQUENCE: 4

Asn Ser Asp Val Gly Ala Tyr Asn Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Light-chain CDR2

<400> SEQUENCE: 5

Asp Val Asn
1

<210> SEQ ID NO 6
<211> LENGTH: 11
<212> TYPE: PRT
<213> ORGANISM: Artificial Sequence
<220> FEATURE:
<223> OTHER INFORMATION: Light-chain CDR3

<400> SEQUENCE: 6

Ala Ala Trp Asp Asp Ser Leu Asn Gly Leu Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Heavy-chain CDR1

<400> SEQUENCE: 7

Gly Tyr Ile Phe Thr Asp Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Heavy-chain CDR2
```

```
<400> SEQUENCE: 8

Ile Asn Pro Tyr Asp Gly Arg Thr
1               5

<210> SEQ ID NO 9
<211> LENGTH: 14
<212> TYPE: PRT
<213> ORGANISM: Artificial Sequence
<220> FEATURE:
<223> OTHER INFORMATION: Heavy-chain CDR3

<400> SEQUENCE: 9

Ala Lys Gln Met Gly Ile Trp Asp Tyr Asp Ala Phe Asp Ile
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Light-chain CDR1

<400> SEQUENCE: 10

Ser Ser Asn Ile Gly Ala Gly Tyr Asp
1               5

<210> SEQ ID NO 11
<211> LENGTH: 3
<212> TYPE: PRT
<213> ORGANISM: Artificial Sequence
<220> FEATURE:
<223> OTHER INFORMATION: Light-chain CDR2

<400> SEQUENCE: 11

Gly Asn Ser
1

<210> SEQ ID NO 12
<211> LENGTH: 11
<212> TYPE: PRT
<213> ORGANISM: Artificial Sequence
<220> FEATURE:
<223> OTHER INFORMATION: Light-chain CDR3

<400> SEQUENCE: 12

Val Ala Trp Asp Asp Ser Leu Lys Ala Tyr Val
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Heavy-chain CDR1

<400> SEQUENCE: 13

Gly Phe Ser Phe His Asp Tyr Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Heavy-chain CDR2

<400> SEQUENCE: 14
```

```
Ile Ser Trp Asp Gly Thr Ile Thr
1               5

<210> SEQ ID NO 15
<211> LENGTH: 15
<212> TYPE: PRT
<213> ORGANISM: Artificial Sequence
<220> FEATURE:
<223> OTHER INFORMATION: Heavy-chain CDR3

<400> SEQUENCE: 15

Ala Lys Glu Asp Arg Tyr Asp Tyr Tyr Ser Gly Ala Phe Asp Ile
1               5                   10                  15

<210> SEQ ID NO 16
<211> LENGTH: 9
<212> TYPE: PRT
<213> ORGANISM: Artificial Sequence
<220> FEATURE:
<223> OTHER INFORMATION: Light-chain CDR1

<400> SEQUENCE: 16

Ser Ser Asp Val Gly Gly Tyr Asp Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: Light-chain CDR2

<400> SEQUENCE: 17

Asp Val Asn
1

<210> SEQ ID NO 18
<211> LENGTH: 11
<212> TYPE: PRT
<213> ORGANISM: Artificial Sequence
<220> FEATURE:
<223> OTHER INFORMATION: Light-chain CDR3

<400> SEQUENCE: 18

Ser Ser Phe Ala Gly Ser Asn Thr Leu Arg Val
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Heavy-chain CDR1

<400> SEQUENCE: 19

Gly Tyr Thr Phe Ser Ser Tyr Trp
1               5

<210> SEQ ID NO 20
<211> LENGTH: 8
<212> TYPE: PRT
<213> ORGANISM: Artificial Sequence
<220> FEATURE:
<223> OTHER INFORMATION: Heavy-chain CDR2

<400> SEQUENCE: 20
```

```
Ile Asn Pro Gly Asn Gly His Thr
1               5
```

<210> SEQ ID NO 21
<211> LENGTH: 17
<212> TYPE: PRT
<213> ORGANISM: Artificial Sequence
<220> FEATURE:
<223> OTHER INFORMATION: Heavy-chain CDR3

<400> SEQUENCE: 21

```
Ala Lys Asp Ile Ala Tyr Tyr Asp Phe Trp Ser Gly Asp Ala Phe Asp
1               5                   10                  15

Leu
```

<210> SEQ ID NO 22
<211> LENGTH: 6
<212> TYPE: PRT
<213> ORGANISM: Artificial Sequence
<220> FEATURE:
<223> OTHER INFORMATION: Light-chain CDR1

<400> SEQUENCE: 22

```
Lys Leu Gly Asn Lys Tyr
1               5
```

<210> SEQ ID NO 23
<211> LENGTH: 3
<212> TYPE: PRT
<213> ORGANISM: Artificial Sequence
<220> FEATURE:
<223> OTHER INFORMATION: Light-chain CDR2

<400> SEQUENCE: 23

```
Gln Asp Asn
1
```

<210> SEQ ID NO 24
<211> LENGTH: 9
<212> TYPE: PRT
<213> ORGANISM: Artificial Sequence
<220> FEATURE:
<223> OTHER INFORMATION: Light-chain CDR3

<400> SEQUENCE: 24

```
Gln Thr Trp Asp Arg Ser Thr Gly Val
1               5
```

<210> SEQ ID NO 25
<211> LENGTH: 121
<212> TYPE: PRT
<213> ORGANISM: Artificial Sequence
<220> FEATURE:
<223> OTHER INFORMATION: VH

<400> SEQUENCE: 25

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Ser Ser Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Ser Tyr Ala Gln Lys Phe
    50                  55                  60
```

Gln Gly Arg Val Thr Ile Thr Ala Asp Gly Ser Met Ser Thr Ala Tyr
65                  70                  75                  80

Met Glu Leu Ser Ser Leu Arg Ser Glu Asp Thr Ala Val Tyr Tyr Cys
            85                  90                  95

Ala Lys Gly Ala Ile Glu Pro Trp Pro Phe Tyr Phe Asp Asn Trp Gly
        100                 105                 110

Gln Gly Thr Leu Val Thr Val Ser Ser
        115                 120

<210> SEQ ID NO 26
<211> LENGTH: 112
<212> TYPE: PRT
<213> ORGANISM: Artificial Sequence
<220> FEATURE:
<223> OTHER INFORMATION: VL

<400> SEQUENCE: 26

Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
            20                  25                  30

Asn Tyr Leu Ser Trp Tyr Gln Gln Leu Pro Gly Arg Ala Pro Lys Val
        35                  40                  45

Ile Ile Tyr Asp Val Asn Lys Arg Pro Ser Gly Val Pro Asp Arg Phe
50                  55                  60

Ser Gly Ser Arg Ser Gly Lys Thr Ala Ser Leu Thr Ile Ser Gly Leu
65                  70                  75                  80

Gln Ala Glu Asp Glu Ala Asp Tyr Tyr Cys Ala Ala Trp Asp Asp Ser
            85                  90                  95

Leu Asn Gly Leu Val Phe Gly Gly Gly Thr Lys Leu Thr Val Leu Gly
        100                 105                 110

<210> SEQ ID NO 27
<211> LENGTH: 121
<212> TYPE: PRT
<213> ORGANISM: Artificial Sequence
<220> FEATURE:
<223> OTHER INFORMATION: VH

<400> SEQUENCE: 27

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Tyr Met His Trp Val Arg Gln Ala Pro Gly Gln Gly Leu Glu Trp Met
        35                  40                  45

Gly Val Ile Asn Pro Tyr Asp Gly Arg Thr Ser Phe Ala Gln Lys Phe
50                  55                  60

Gln Gly Arg Leu Thr Val Thr Arg Asp Thr Ser Thr Ser Thr Ala Tyr
65                  70                  75                  80

Met Asp Leu Ser Gly Leu Arg Ser Glu Asp Thr Ala Val Tyr Tyr Cys
            85                  90                  95

Ala Lys Gln Met Gly Ile Trp Asp Tyr Asp Ala Phe Asp Ile Trp Gly
        100                 105                 110

Gln Gly Thr Met Val Thr Val Ser Ser
        115                 120

<210> SEQ ID NO 28

```
<211> LENGTH: 112
<212> TYPE: PRT
<213> ORGANISM: Artificial Sequence
<220> FEATURE:
<223> OTHER INFORMATION: VL

<400> SEQUENCE: 28

Gln Phe Val Leu Thr Gln Pro Ser Ser Val Ser Gly Ala Pro Gly Gln
1               5                   10                  15

Arg Val Ile Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Val
        35                  40                  45

Leu Ile Tyr Gly Asn Ser Asp Arg Pro Ser Gly Val Pro Asp Arg Phe
    50                  55                  60

Ser Ala Ser Lys Ser Ala Thr Ser Ala Ser Leu Ala Ile Thr Gly Leu
65                  70                  75                  80

Gln Ala Glu Asp Glu Ala Asp Tyr Tyr Cys Val Ala Trp Asp Ser
                85                  90                  95

Leu Lys Ala Tyr Val Phe Gly Thr Gly Thr Lys Val Thr Val Leu Gly
            100                 105                 110

<210> SEQ ID NO 29
<211> LENGTH: 122
<212> TYPE: PRT
<213> ORGANISM: Artificial Sequence
<220> FEATURE:
<223> OTHER INFORMATION: VH

<400> SEQUENCE: 29

Gln Met Gln Leu Val Glu Ser Gly Gly Gly Leu Val Glu Pro Gly Arg
1               5                   10                  15

Ser Leu Arg Leu Ser Cys Thr Thr Ser Gly Phe Ser Phe His Asp Tyr
            20                  25                  30

Thr Met Tyr Trp Val Arg Gln Val Pro Gly Lys Gly Leu Glu Trp Val
        35                  40                  45

Ser Leu Ile Ser Trp Asp Gly Thr Ile Thr Phe Tyr Ala Asp Pro Val
    50                  55                  60

Arg Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Glu Asp Arg Tyr Asp Tyr Ser Gly Ala Phe Asp Ile Trp
            100                 105                 110

Gly Gln Gly Thr Val Val Thr Val Ser Ser
        115                 120

<210> SEQ ID NO 30
<211> LENGTH: 112
<212> TYPE: PRT
<213> ORGANISM: Artificial Sequence
<220> FEATURE:
<223> OTHER INFORMATION: VL

<400> SEQUENCE: 30

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30
```

```
Asp Tyr Val Ser Trp Tyr Gln Gln His Pro Gly Lys Ala Pro Lys Leu
            35                  40                  45

Ile Leu Asn Asp Val Asn Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Pro Asp Asp Glu Ala Asp Tyr Tyr Cys Ser Ser Phe Ala Gly Ser
                 85                  90                  95

Asn Thr Leu Arg Val Phe Gly Gly Gly Thr Lys Leu Thr Val Leu Gly
            100                 105                 110

<210> SEQ ID NO 31
<211> LENGTH: 124
<212> TYPE: PRT
<213> ORGANISM: Artificial Sequence
<220> FEATURE:
<223> OTHER INFORMATION: VH

<400> SEQUENCE: 31

Gln Val Gln Leu Val Gln Ser Gly Ala Glu Val Lys Lys Pro Gly Ala
 1               5                   10                  15

Ser Val Lys Leu Ser Cys Lys Ala Ser Gly Tyr Thr Phe Ser Ser Tyr
             20                  25                  30

Trp Met His Trp Val Arg Gln Ala Pro Gly Gln Arg Leu Glu Trp Met
            35                  40                  45

Gly Glu Ile Asn Pro Gly Asn Gly His Thr Asn Tyr Asn Glu Lys Phe
 50                  55                  60

Lys Ser Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Asp Ile Ala Tyr Tyr Asp Phe Trp Ser Gly Asp Ala Phe Asp
            100                 105                 110

Leu Trp Gly Gln Gly Thr Met Val Thr Val Ser Ser
            115                 120

<210> SEQ ID NO 32
<211> LENGTH: 107
<212> TYPE: PRT
<213> ORGANISM: Artificial Sequence
<220> FEATURE:
<223> OTHER INFORMATION: VL

<400> SEQUENCE: 32

Ser Tyr Glu Leu Thr Gln Pro Leu Ser Val Ser Val Ser Pro Gly Gln
 1               5                   10                  15

Thr Ala Ser Ile Thr Cys Ser Gly Asp Lys Leu Gly Asn Lys Tyr Ala
             20                  25                  30

Ser Trp Tyr Gln Gln Lys Pro Gly Gln Ser Pro Val Leu Val Ile Tyr
            35                  40                  45

Gln Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Thr
 65                  70                  75                  80

Asp Glu Ala Asp Tyr Tyr Cys Gln Thr Trp Asp Arg Ser Thr Gly Val
                 85                  90                  95

Phe Gly Thr Gly Thr Lys Val Thr Val Leu Gly
            100                 105
```

<210> SEQ ID NO 33
<211> LENGTH: 11
<212> TYPE: PRT
<213> ORGANISM: Artificial Sequence
<220> FEATURE:
<223> OTHER INFORMATION: Light chain CDR3

<400> SEQUENCE: 33

Ala Ala Trp Asp Asp Leu Asn Gly Leu Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Light chain CDR3

<400> SEQUENCE: 34

Ala Ala Trp Asp Asp Ser Leu Ile Gly His Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Light chain CDR3

<400> SEQUENCE: 35

Ala Ala Trp Asp Asp Asn Leu Asn Gly Leu Val
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Light chain CDR3

<400> SEQUENCE: 36

Ala Ala Trp Asp Asp Ser Leu Tyr Gly Leu Val
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Light chain CDR3

<400> SEQUENCE: 37

Ala Ala Trp Asp Asp Ser Leu Asn Asp Leu Val
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Light chain CDR3

<400> SEQUENCE: 38

Ala Ala Trp Asp Asp Ser Leu Asn Val Leu Val
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Light chain CDR3

<400> SEQUENCE: 39

```
Ala Ala Trp Asp Asp Asn Ser Asp Phe His Val
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: Light chain CDR3

<400> SEQUENCE: 40

```
Ala Ala Trp Asp Asp Asn Leu Tyr Gly Leu Val
1               5                   10
```

<210> SEQ ID NO 41
<211> LENGTH: 112
<212> TYPE: PRT
<213> ORGANISM: Artificial Sequence
<220> FEATURE:
<223> OTHER INFORMATION: VL

<400> SEQUENCE: 41

```
Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
            20                  25                  30

Asn Tyr Leu Ser Trp Tyr Gln Gln Leu Pro Gly Arg Ala Pro Lys Val
        35                  40                  45

Ile Ile Tyr Asp Val Asn Lys Arg Pro Ser Gly Val Pro Asp Arg Phe
    50                  55                  60

Ser Gly Ser Arg Ser Gly Lys Thr Ala Ser Leu Thr Ile Ser Gly Leu
65                  70                  75                  80

Gln Ala Glu Asp Glu Ala Asp Tyr Tyr Cys Ala Ala Trp Asp Asp
                85                  90                  95

Leu Asn Gly Leu Val Phe Gly Gly Gly Thr Lys Leu Thr Val Leu Gly
            100                 105                 110
```

<210> SEQ ID NO 42
<211> LENGTH: 112
<212> TYPE: PRT
<213> ORGANISM: Artificial Sequence
<220> FEATURE:
<223> OTHER INFORMATION: VL

<400> SEQUENCE: 42

```
Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
            20                  25                  30

Asn Tyr Leu Ser Trp Tyr Gln Gln Leu Pro Gly Arg Ala Pro Lys Val
        35                  40                  45

Ile Ile Tyr Asp Val Asn Lys Arg Pro Ser Gly Val Pro Asp Arg Phe
    50                  55                  60
```

```
Ser Gly Ser Arg Ser Gly Lys Thr Ala Ser Leu Thr Ile Ser Gly Leu
 65                  70                  75                  80

Gln Ala Glu Asp Glu Ala Asp Tyr Tyr Cys Ala Ala Trp Asp Asp Ser
                 85                  90                  95

Leu Ile Gly His Val Phe Gly Gly Gly Thr Lys Leu Thr Val Leu Gly
            100                 105                 110
```

<210> SEQ ID NO 43
<211> LENGTH: 112
<212> TYPE: PRT
<213> ORGANISM: Artificial Sequence
<220> FEATURE:
<223> OTHER INFORMATION: VL

<400> SEQUENCE: 43

```
Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
                20                  25                  30

Asn Tyr Leu Ser Trp Tyr Gln Gln Leu Pro Gly Arg Ala Pro Lys Val
            35                  40                  45

Ile Ile Tyr Asp Val Asn Lys Arg Pro Ser Gly Val Pro Asp Arg Phe
     50                  55                  60

Ser Gly Ser Arg Ser Gly Lys Thr Ala Ser Leu Thr Ile Ser Gly Leu
 65                  70                  75                  80

Gln Ala Glu Asp Glu Ala Asp Tyr Tyr Cys Ala Ala Trp Asp Asp Asn
                 85                  90                  95

Leu Asn Gly Leu Val Phe Gly Gly Gly Thr Lys Leu Thr Val Leu Gly
            100                 105                 110
```

<210> SEQ ID NO 44
<211> LENGTH: 112
<212> TYPE: PRT
<213> ORGANISM: Artificial Sequence
<220> FEATURE:
<223> OTHER INFORMATION: VL

<400> SEQUENCE: 44

```
Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
                20                  25                  30

Asn Tyr Leu Ser Trp Tyr Gln Gln Leu Pro Gly Arg Ala Pro Lys Val
            35                  40                  45

Ile Ile Tyr Asp Val Asn Lys Arg Pro Ser Gly Val Pro Asp Arg Phe
     50                  55                  60

Ser Gly Ser Arg Ser Gly Lys Thr Ala Ser Leu Thr Ile Ser Gly Leu
 65                  70                  75                  80

Gln Ala Glu Asp Glu Ala Asp Tyr Tyr Cys Ala Ala Trp Asp Asp Ser
                 85                  90                  95

Leu Tyr Gly Leu Val Phe Gly Gly Gly Thr Lys Leu Thr Val Leu Gly
            100                 105                 110
```

<210> SEQ ID NO 45
<211> LENGTH: 112
<212> TYPE: PRT
<213> ORGANISM: Artificial Sequence
<220> FEATURE:
<223> OTHER INFORMATION: VL

<400> SEQUENCE: 45

Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
            20                  25                  30

Asn Tyr Leu Ser Trp Tyr Gln Gln Leu Pro Gly Arg Ala Pro Lys Val
        35                  40                  45

Ile Ile Tyr Asp Val Asn Lys Arg Pro Ser Gly Val Pro Asp Arg Phe
    50                  55                  60

Ser Gly Ser Arg Ser Gly Lys Thr Ala Ser Leu Thr Ile Ser Gly Leu
65                  70                  75                  80

Gln Ala Glu Asp Glu Ala Asp Tyr Tyr Cys Ala Ala Trp Asp Asp Ser
                85                  90                  95

Leu Asn Asp Leu Val Phe Gly Gly Gly Thr Lys Leu Thr Val Leu Gly
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: VL

<400> SEQUENCE: 46

Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
            20                  25                  30

Asn Tyr Leu Ser Trp Tyr Gln Gln Leu Pro Gly Arg Ala Pro Lys Val
        35                  40                  45

Ile Ile Tyr Asp Val Asn Lys Arg Pro Ser Gly Val Pro Asp Arg Phe
    50                  55                  60

Ser Gly Ser Arg Ser Gly Lys Thr Ala Ser Leu Thr Ile Ser Gly Leu
65                  70                  75                  80

Gln Ala Glu Asp Glu Ala Asp Tyr Tyr Cys Ala Ala Trp Asp Asp Ser
                85                  90                  95

Leu Asn Val Leu Val Phe Gly Gly Gly Thr Lys Leu Thr Val Leu Gly
            100                 105                 110

<210> SEQ ID NO 47
<211> LENGTH: 112
<212> TYPE: PRT
<213> ORGANISM: Artificial Sequence
<220> FEATURE:
<223> OTHER INFORMATION: VL

<400> SEQUENCE: 47

Gln Leu Val Leu Thr Gln Pro Arg Ser Val Ser Gly Ser Pro Gly Gln
1               5                   10                  15

Ser Val Thr Ile Ser Cys Thr Gly Thr Gly Thr Asn Ser Asp Val Gly Ala Tyr
            20                  25                  30

Asn Tyr Leu Ser Trp Tyr Gln Gln Leu Pro Gly Arg Ala Pro Lys Val
        35                  40                  45

Ile Ile Tyr Asp Val Asn Lys Arg Pro Ser Gly Val Pro Asp Arg Phe
    50                  55                  60

Ser Gly Ser Arg Ser Gly Lys Thr Ala Ser Leu Thr Ile Ser Gly Leu
65                  70                  75                  80

```
Gln Ala Glu Asp Glu Ala Asp Tyr Tyr Cys Ala Ala Trp Asp Asp Asn
                85                  90                  95

Ser Asp Phe His Val Phe Gly Gly Gly Thr Lys Leu Thr Val Leu Gly
            100                 105                 110
```

<210> SEQ ID NO 48
<211> LENGTH: 112
<212> TYPE: PRT
<213> ORGANISM: Artificial Sequence
<220> FEATURE:
<223> OTHER INFORMATION: VL

<400> SEQUENCE: 48

```
Gln Leu Val Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
            20                  25                  30

Asn Tyr Leu Ser Trp Tyr Gln Gln Leu Pro Gly Arg Ala Pro Lys Val
        35                  40                  45

Ile Ile Tyr Asp Val Asn Lys Arg Pro Ser Gly Val Pro Asp Arg Phe
    50                  55                  60

Ser Gly Ser Arg Ser Gly Lys Thr Ala Ser Leu Thr Ile Ser Gly Leu
65                  70                  75                  80

Gln Ala Glu Asp Glu Ala Asp Tyr Tyr Cys Ala Ala Trp Asp Asp Asn
                85                  90                  95

Leu Tyr Gly Leu Val Phe Gly Gly Gly Thr Lys Leu Thr Val Leu Gly
            100                 105                 110
```

<210> SEQ ID NO 49
<211> LENGTH: 121
<212> TYPE: PRT
<213> ORGANISM: Artificial Sequence
<220> FEATURE:
<223> OTHER INFORMATION: VH

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Ser Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Ser Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Ala Ile Glu Pro Trp Pro Phe Tyr Phe Asp Asn Trp Gly
            100                 105                 110

Gln Gly Thr Leu Val Thr Val Ser Ser
            115                 120
```

<210> SEQ ID NO 50
<211> LENGTH: 111
<212> TYPE: PRT
<213> ORGANISM: Artificial Sequence
<220> FEATURE:
<223> OTHER INFORMATION: VL

```
<400> SEQUENCE: 50

Gln Ser Ala Leu Thr Gln Pro Arg Ser Val Ser Gly Ser Pro Gly Gln
1               5                   10                  15

Ser Val Thr Ile Ser Cys Thr Gly Thr Asn Ser Asp Val Gly Ala Tyr
                20                  25                  30

Asn Tyr Leu Ser Trp Tyr Gln Gln Leu Pro Gly Arg Ala Pro Lys Val
            35                  40                  45

Ile Ile Tyr Asp Val Asn Lys Arg Pro Ser Gly Val Pro Asp Arg Phe
        50                  55                  60

Ser Gly Ser Arg Ser Gly Lys Thr Ala Ser Leu Thr Ile Ser Gly Leu
65                  70                  75                  80

Gln Ala Glu Asp Glu Ala Asp Tyr Tyr Cys Ala Ala Trp Asp Asp Asn
                85                  90                  95

Leu Tyr Gly Leu Val Phe Gly Gly Gly Thr Lys Leu Thr Val Leu
            100                 105                 110
```